(12) United States Patent  
Nakamura et al.

(10) Patent No.: US 11,774,606 B2  
(45) Date of Patent: Oct. 3, 2023

(54) ELECTROMAGNETIC WAVE DETECTOR, ELECTROMAGNETIC WAVE DETECTION APPARATUS, INSPECTION APPARATUS, AND CIRCUIT BOARD

(71) Applicant: CANON COMPONENTS, INC., Saitama-ken (JP)

(72) Inventors: Takehiro Nakamura, Saitama-ken (JP); Ryouta Saruya, Saitama-ken (JP)

(73) Assignee: CANON COMPONENTS, INC., Saitama (JP)

( * ) Notice: Subject to any disclaimer, the term of this patent is extended or adjusted under 35 U.S.C. 154(b) by 0 days.

(21) Appl. No.: 17/674,103

(22) Filed: Feb. 17, 2022

(65) Prior Publication Data

US 2022/0171078 A1 Jun. 2, 2022

Related U.S. Application Data

(63) Continuation of application No. PCT/JP2020/032429, filed on Aug. 27, 2020.

(30) Foreign Application Priority Data

Aug. 30, 2019 (JP) ................................. 2019-158860  
Aug. 30, 2019 (JP) ................................. 2019-158861  
Aug. 30, 2019 (JP) ................................. 2019-158862

(51) Int. Cl.  
*G01T 1/20* (2006.01)

(52) U.S. Cl.  
CPC .......... *G01T 1/2002* (2013.01); *G01T 1/2006* (2013.01)

(58) Field of Classification Search  
CPC . G01T 1/2002; G01T 1/2006; G01T 1/20186; A61B 6/00; G01J 1/02;

(Continued)

(56) References Cited

U.S. PATENT DOCUMENTS 6,479,827 B1 11/2002 Hamamoto  
7,042,000 B2 5/2006 Yasuda  
(Continued)

FOREIGN PATENT DOCUMENTS

JP H0511060 A 1/1993  
JP 2001078099 A 3/2001  
(Continued)

OTHER PUBLICATIONS

International Search Report issued in Intl. Appln. No PCT/JP2020/032429 dated Oct. 27, 2020 English translation provided.

(Continued)

*Primary Examiner* — Kiho Kim  
(74) *Attorney, Agent, or Firm* — ROSSI, KIMMS & McDOWELL LLP

(57) ABSTRACT

An electromagnetic wave detector is provided. The electromagnetic wave detector comprises: a base; a sensor element arranged on a principal surface of the base and configured to convert, into an electrical signal, light emitted from a scintillator which receives an electromagnetic wave; a lens portion arranged between the scintillator and the sensor element and configured to collect the light generated by the scintillator to the sensor element; a light transmissive portion arranged between the lens portion and the sensor element and configured to transmit the light generated by the scintillator; and a shielding portion including an inner wall located on a periphery of the sensor element and configured to shield the electromagnetic wave. The inner wall is arranged between the light transmissive portion and the principal surface.

22 Claims, 19 Drawing Sheets

(58) Field of Classification Search
CPC ........ G01N 23/04; G01N 23/18; H01L 23/02; H01L 23/12
See application file for complete search history.

(56) References Cited

U.S. PATENT DOCUMENTS

| | | | |
|---|---|---|---|
| 7,148,464 B2 | 12/2006 | Shibayama | |
| 7,349,626 B2 | 3/2008 | Nishizawa | |
| 2015/0247936 A1 | 9/2015 | Gemma | |
| 2018/0246228 A1* | 8/2018 | Nakamura | .......... G01T 1/20188 |

FOREIGN PATENT DOCUMENTS

| | | | | | |
|---|---|---|---|---|---|
| JP | 2004163895 A | | 6/2004 | | |
| JP | 2004327914 A | | 11/2004 | | |
| JP | 2006329905 A | | 12/2006 | | |
| JP | 2008051626 A | | 3/2008 | | |
| JP | 2012090770 A | | 5/2012 | | |
| JP | 2015180239 A | | 10/2015 | | |
| JP | 2018115953 A | * | 7/2018 | ........... E01D 15/127 | |
| JP | 2018141781 A | | 9/2018 | | |
| WO | 2004019411 A1 | | 3/2004 | | |

OTHER PUBLICATIONS

Written Opinion issued in Intl. Appln. No. PCT/JP2020/032429 dated Oct. 27, 2020.

* cited by examiner

FIG. 9C

| ELEVATION ANGLE [°] | SCATTERED RAY INTENSITY COMPARISON |
|---|---|
| 5 | 0.00 |
| 10 | 0.00 |
| 15 | 0.63 |
| 20 | 0.70 |
| 25 | 0.95 |
| 30 | 1.00 |
| 35 | 0.73 |
| 40 | 0.61 |
| 45 | 0.43 |
| 50 | 0.28 |
| 55 | 0.10 |
| 60 | 0.12 |

ELECTROMAGNETIC WAVE DETECTOR, ELECTROMAGNETIC WAVE DETECTION APPARATUS, INSPECTION APPARATUS, AND CIRCUIT BOARD

CROSS-REFERENCE TO RELATED APPLICATION(S)

This application is a continuation of International Patent Application No. PCT/JP2020/032429 filed on Aug. 27, 2020, which claims priority to and the benefit of Japanese Patent Application Nos. 2019-158860, 2019-158861 and 2019-158862 filed on Aug. 30, 2019, the entire disclosures of which are incorporated herein by reference.

BACKGROUND OF THE INVENTION

Field of the Invention

The present invention relates to an electromagnetic wave detector, an electromagnetic wave detection apparatus, an inspection apparatus, and a circuit board.

Background Art

In an electromagnetic wave detector, when a sensor element for detecting an electromagnetic wave is irradiated with an electromagnetic wave such as radiation, the sensor element may be damaged. PTL 1 describes a line sensor including a scintillator that receives radiation and emits light and a two-dimensional light-receiving element arranged in a bent direction from a direction in which radiation enters the scintillator. By preventing the light-receiving element from being irradiated with radiation directly, damage to the light-receiving element can be suppressed.

CITATION LIST

Patent Literature

PTL 1: Japanese Patent Laid-Open No. 2006-329905
PTL 2: Japanese Patent Laid-Open No. 2015-180239

In an arrangement described in PTL 1, a scattered ray of radiation entering the scintillator, which is scattered without being absorbed by the scintillator, may enter the light-receiving element. If the scattered ray enters the light-receiving element, the light-receiving element may be damaged due to the incidence of the scattered ray.

The present invention provides a technique advantageous in suppressing damage to a sensor element caused by an electromagnetic wave in an electromagnetic wave detector.

SUMMARY OF THE INVENTION

According to some embodiments, an electromagnetic wave detector comprising: a base; a sensor element arranged on a principal surface of the base and configured to convert, into an electrical signal, light emitted from a scintillator which receives an electromagnetic wave; a lens portion arranged between the scintillator and the sensor element and configured to collect the light generated by the scintillator to the sensor element; a light transmissive portion arranged between the lens portion and the sensor element and configured to transmit the light generated by the scintillator; and a shielding portion including an inner wall located on a periphery of the sensor element and configured to shield the electromagnetic wave, wherein the inner wall is arranged between the light transmissive portion and the principal surface, is provided.

According to some other embodiments, an electromagnetic wave detector comprising: a base; a sensor element arranged on a principal surface of the base and configured to convert, into an electrical signal, light emitted from a scintillator which receives an electromagnetic wave; a lens portion arranged between the scintillator and the sensor element and configured to collect the light generated by the scintillator to the sensor element; and a light transmissive portion arranged between the lens portion and the sensor element and configured to transmit the light generated by the scintillator, wherein the sensor element is arranged at a position not overlapping an optical axis of the lens portion, and the light transmissive portion has an effect of refracting a light beam, that has been generated by the scintillator and passed through the optical axis of the lens portion, to enter the sensor element, is provided.

According to still other embodiments, a circuit board comprising a mounting surface on which an integrated circuit is mounted and at least one wiring layer, wherein in an orthogonal projection with respect to the mounting surface, a first layer of the at least one wiring layer is a wiring layer in which a ratio of an area of a portion, where a conductor forming a wiring pattern is arranged, with respect to a region overlapping the integrated circuit is not higher than 20%, is provided.

According to yet other embodiments, an electromagnetic wave detector comprising: a scintillator extending along a first axis; a first line sensor extending along a second axis parallel to the first axis and configured to detect light from a first region of the scintillator; and a second line sensor extending along a third axis parallel to the first axis and different from the second axis, and configured to detect light from a second region of the scintillator, is provided.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 9C is a table showing the angle dependency of the scattered ray.

DESCRIPTION OF THE EMBODIMENTS

Figure 1:
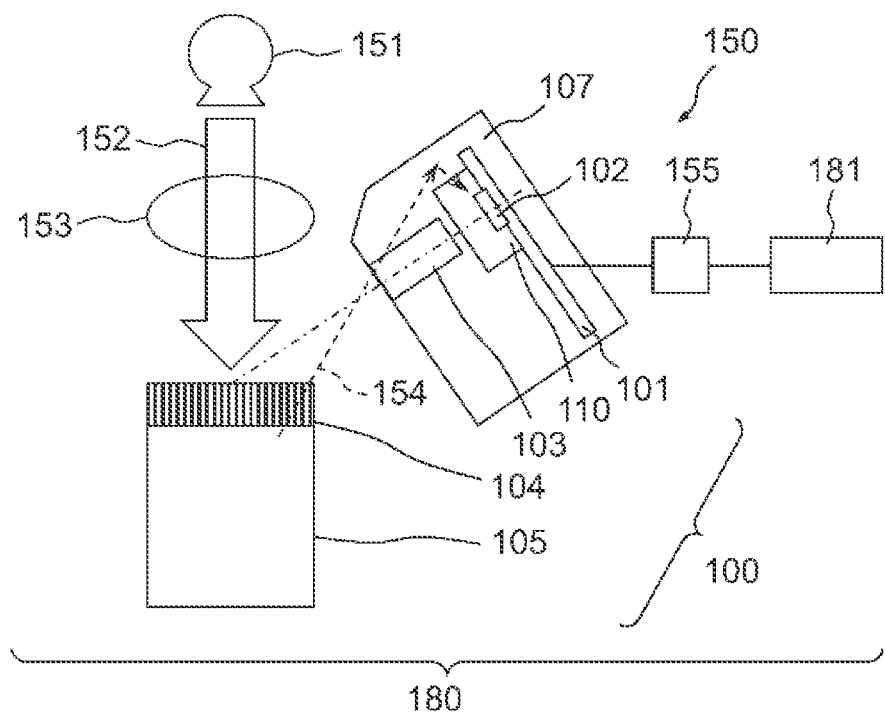
FIG. 1 is a view showing an example of the arrangement of a radiation detection apparatus using a radiation detector and an inspection apparatus including the radiation detection apparatus according to an embodiment.

Hereinafter, embodiments will be described in detail with reference to the attached drawings. Note, the following embodiments are not intended to limit the scope of the claimed invention, and limitation is not made an invention that requires a combination of all features described in the embodiments. Two or more of the multiple features described in the embodiments may be combined as appropriate. Furthermore, the same reference numerals are given to the same or similar configurations, and redundant description thereof is omitted.

Figure 2:
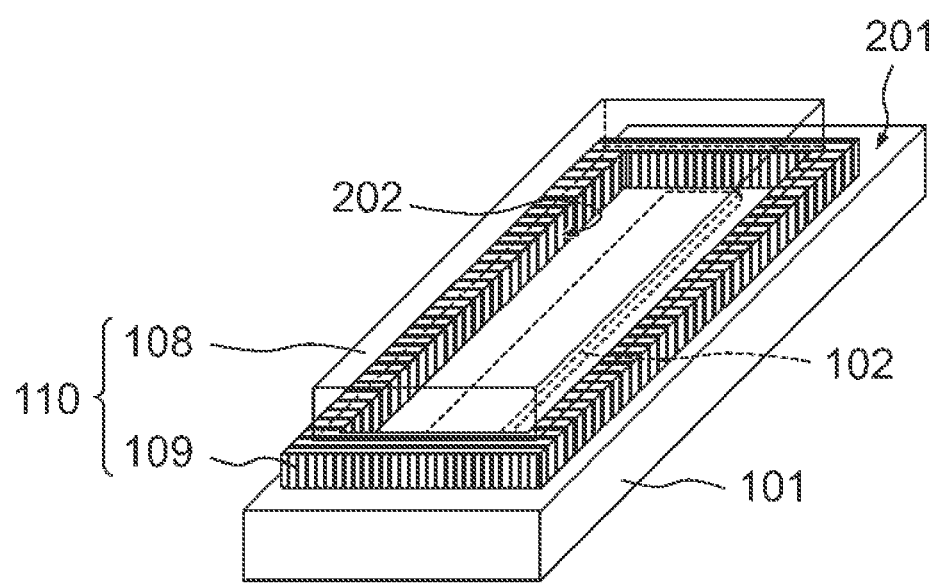
FIG. 2 is a perspective view showing an example of the arrangement of a covering portion that covers a sensor element of the radiation detector shown in FIG. 1.

A radiation detector as an embodiment of an electromagnetic wave detector will be described with reference to FIGS. 1 to 15B. FIG. 1 is a view showing an example of the arrangement of a radiation detection apparatus 150 using a radiation detector 100 and an inspection apparatus 180 including the radiation detection apparatus 150 according to this embodiment. FIG. 2 is an enlarged perspective view of the periphery of a covering portion 110 covering a sensor element 102 of the radiation detector 100.

In the radiation detector 100, a scintillator 104 converts incident radiation into light, and the sensor element 102 converts the converted light into an electrical signal. Details of the radiation detector 100 will be described later. The radiation detector 100 forms the radiation detection apparatus 150 together with a radiation source 151 (electromagnetic wave source) for emitting radiation 152. The radiation detection apparatus 150 generates an image (radiation image) of an object 153 arranged between the radiation source 151 and the radiation detector 100. In the radiation detection apparatus 150, for example, an image generation processor 155 generates a radiation image based on the electrical signal acquired by the sensor element 102 of the radiation detector 100. As shown in, for example, FIG. 1, the image generation processor 155 may be implemented in an external computer to which the electrical signal acquired by the sensor element 102 is transmitted, or the like. Alternatively, for example, the image generation processor 155 may be integrated with the sensor element 102 mounted on a base 101.

A determiner 181 that determines the quality of the object 153 using the radiation image data generated by the radiation detection apparatus 150 including the radiation detector 100 according to this embodiment may be combined with the radiation detection apparatus 150, thereby forming the inspection apparatus 180. The inspection apparatus 180 may be an inspection apparatus that includes, for example, the linear scintillator 104 and the linear sensor element 102 (for example, a line sensor) and inspects the object 153 moving between the radiation source 151 and the radiation detector 100.

The radiation detector 100 according to this embodiment will be described next. The radiation detector 100 includes the base 101, the sensor element 102, the covering portion 110, a lens portion 103, and the scintillator 104

The scintillator 104 converts the radiation 152 entering from the radiation source 151 via the object 153 into light detectable by the sensor element 102. For example, the scintillator 104 generates light of a wavelength of 350 nm to 800 nm with a luminance corresponding to the dose of the incident radiation 152. As shown in FIG. 1, the scintillator 104 may be arranged on a scintillator base 105. In this case, the radiation detector 100 can include the scintillator base 105.

The sensor element 102 is arranged on the principal surface 201 of the base 101, and converts the light generated by the scintillator 104 into an electrical signal. The sensor element 102 can include, for example, a photoelectric conversion element and a switch element formed on a semiconductor substrate made of silicon or the like. The sensor element 102 may be a linear sensor element including a longitudinal direction (main scanning direction) and a widthwise direction (sub-scanning direction) orthogonal to the longitudinal direction, as shown in FIG. 2. The base 101 on which the sensor element 102 is mounted can be a printed circuit board on which a wiring pattern is formed.

The lens portion 103 is arranged between the scintillator 104 and the sensor element 102, and collects the light generated by the scintillator 104 to the sensor element. As the lens portion 103, a rod lens array in which a plurality of lens elements are one- or two-dimensionally arranged may be used. As a rod lens, for example, a SELFOC® lens or the like can be used.

The covering portion 110 is arranged between the lens portion 103 and the sensor element 102 to cover the sensor element 102. As shown in FIG. 2, the covering portion 110 includes a light transmissive portion 108 and a shielding portion 109. The light transmissive portion 108 is arranged between the lens portion 103 and the sensor element 102, and transmits the light generated by the scintillator 104. The shielding portion 109 includes inner walls 202 located on the periphery of the sensor element 102, and shields radiation (X-rays) (serves as one of absorbing, attenuating, and reflecting functions). The inner walls 202 are arranged between the light transmissive portion 108 and a principal surface 201 of the base 101. As shown in FIG. 2, the shielding portion 109 may be arranged on the principal surface 201 of the base 101.

The positional relationship among the base 101, the sensor element 102, the covering portion 110, and the lens portion 103 can be fixed by a housing 107. The housing 107 need only support and fix the respective components arranged in the housing 107, and may be made of a metal or resin. The housing 107 may contain, for example, a metal such as lead to protect the sensor element 102 and the like from the radiation 152.

In the arrangement shown in FIG. 1, the radiation 152 emitted from the radiation source 151 to the scintillator 104 of the radiation detector 100 via the object 153 is configured not to directly enter the sensor element 102. More specifically, the sensor element 102 arranged at a position away from the optical axis of the radiation 152 converts, into an electrical signal, the light generated by the scintillator 104 due to the incidence of the radiation 152. This can suppress damage to the sensor element 102 by the radiation 152.

However, the radiation 152 which has entered the scintillator 104 of the radiation detector 100 via the object 153 may be scattered in the scintillator 104 or the scintillator base 105 supporting the scintillator 104, thereby generating a scattered ray 154. The scattered ray 154 may pass through the lens portion 103 to enter the sensor element 102. Furthermore, the scattered ray 154 may further be scattered in the housing 107 or the like to enter the sensor element 102. If the scattered ray 154 enters the sensor element 102, the sensor element 102 unwantedly detects the scattered ray 154, thereby degrading the image quality of the generated radiation image. In addition, the sensor element 102 may be damaged by the scattered ray 154. Next, the arrangement of the light transmissive portion 108 and the shielding portion 109 of the covering portion 110 for suppressing the influence of the scattered ray 154 on the sensor element 102 will be described.

The light transmissive portion 108 is made of a material that can transmit the light generated by the scintillator 104. For example, the light transmissive portion 108 may transmit 80% or more of the light generated by the scintillator 104. Furthermore, for example, the light transmissive portion 108 may transmit 90% or more of the light generated by the scintillator 104. If the light transmissive portion 108 has a thickness to some extent, it can suppress incidence of radiation such as X-rays. The light transmissive portion 108 may be, for example, glass of about 3 mm to 5 mm. For the thickness, an appropriate thickness is set in accordance with the focal length of the lens portion 103 and the like. At this time, glass may be added with at least one of lead and bismuth. By adding a metal such as lead or bismuth to glass, it is possible to largely suppress radiation from passing through the light transmissive portion 108.

The shielding portion 109 is arranged to suppress the scattered ray 154 scattered in the housing 107 or the like from entering the sensor element 102 at an angle close to a direction along the principal surface 201 of the base 101. A component of the scattered ray 154 entering at an angle close to the normal direction of the principal surface 201 of the base 101 can be suppressed by the above-described light transmissive portion 108 from entering the sensor element 102. Because of multiple scattering of radiation, it is difficult to predict the trajectory. By arranging not only the light transmissive portion 108 but also the shielding portion 109 at a position close to the sensor element 102, it is possible to effectively suppress the incidence of the scattered ray 154 (radiation) on the sensor element 102.

If a material with a larger atomic number or a material with large specific gravity is used for the shielding portion 109, the shielding portion 109 can shield radiation more. As shown in FIG. 2, the shielding portion 109 can be arranged on the principal surface 201 of the base 101. Since, as described above, a printed circuit board or the like may be used as the base 101, the shielding portion 109 may have an insulating property. For example, a resin sheet or the like may be used as the shielding portion 109. More specifically, a resin containing a metal may be used for the shielding portion 109. By adding a metal such as lead, bismuth, or tungsten to a resin, it is possible to suppress radiation from passing through the shielding portion 109. For example, the shielding portion 109 may be a resin sheet containing tungsten. The shielding portion 109 may be an elastic body. If the shielding portion 109 is an elastic body, the adhesion between the shielding portion 109 and the light transmissive portion 108 and the adhesion between the shielding portion 109 and the base 101 improve, thereby making it possible to suppress not only the incidence of the scattered ray 154 but also entering of particles into the covering portion 110 and the like. This can further improve the reliability of the radiation detector 100. For example, as shown in FIG. 2, the sensor element 102 may be sealed by the principal surface 201 of the base 101, the light transmissive portion 108, and the shielding portion 109. That is, the sensor element 102 may be surrounded by the inner walls 202 of the shielding portion 109. However, the present invention is not limited to this, and when the inner walls 202 of the shielding portion 109 are arranged on at least part of the periphery of the sensor element 102, it is possible to suppress the scattered ray 154 entering the sensor element 102 at an angle close to the direction along the principal surface 201 of the base 101.

Figure 3A:
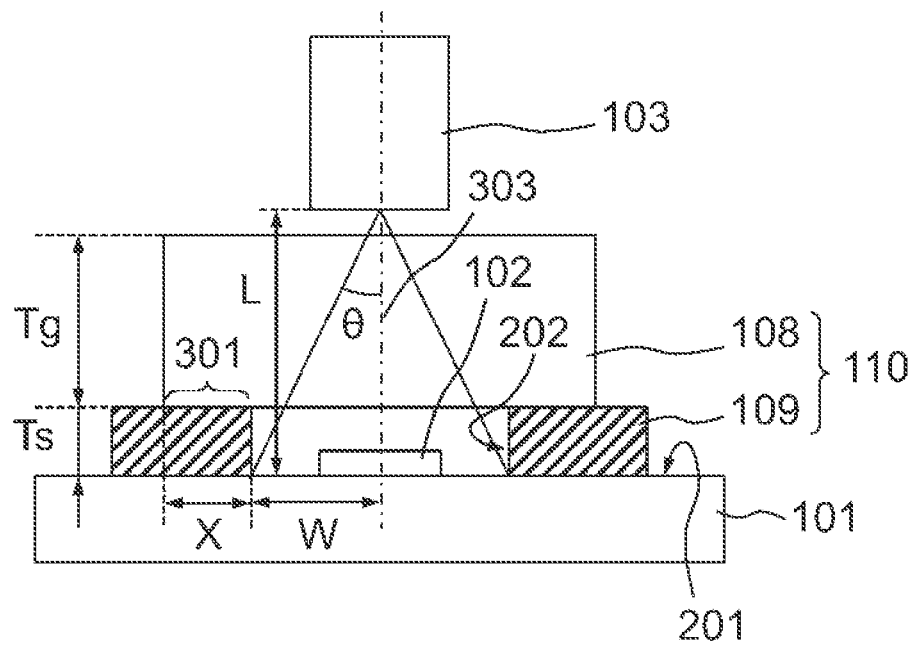
FIG. 3A is a sectional view showing an example of the arrangement of the covering portion shown in FIG. 2.
Figure 3B:
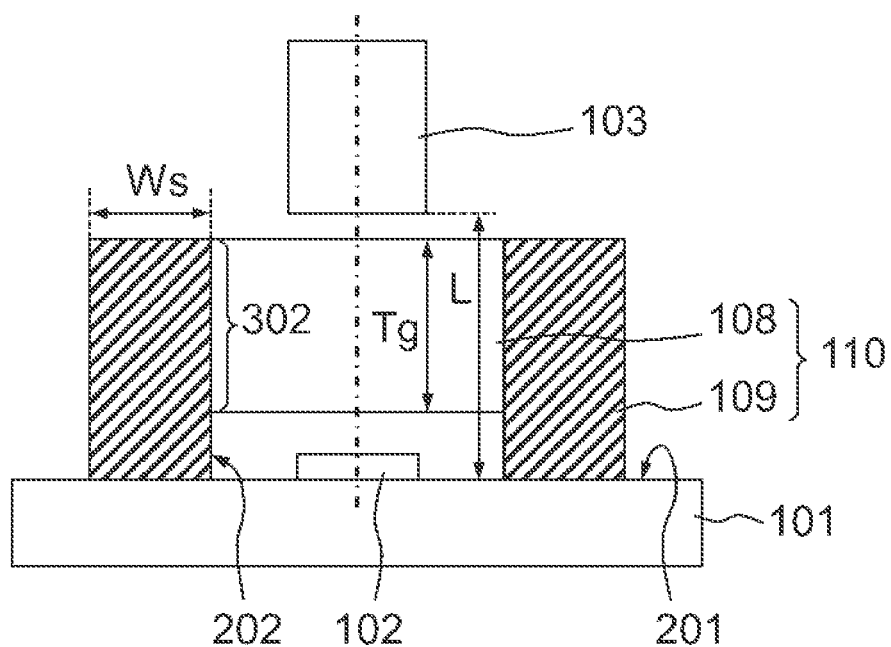
FIG. 3B is a sectional view showing an example of the arrangement of the covering portion shown in FIG. 2.

The arrangement of the light transmissive portion 108 and the shielding portion 109 will be described next with reference to FIGS. 3A and 3B. FIGS. 3A and 3B are sectional views, in the widthwise direction, of the base 101, the sensor element 102, and the covering portion 110 shown in FIG. 2.

In the arrangement shown in FIG. 3A, an upper surface of the shielding portion 109 on the opposite side of a surface contacting the principal surface 201 of the base 101 and an opposite surface of the light transmissive portion 108 facing the principal surface 201 of the base 101 are in contact with each other. In an orthogonal projection with respect to the principal surface 201 of the base 101, a contact portion 301 between the upper surface of the shielding portion 109 and the opposite surface of the light transmissive portion 108 may surround the sensor element 102. That is, the shielding portion 109 may be used as a support body, and the light transmissive portion 108 may be placed on the upper surface of the shielding portion 109. As shown in FIG. 3A, μg represents the mass absorption coefficient of the light transmissive portion 108, μs represents the mass absorption coefficient of the shielding portion 109, and in a section passing through the sensor element 102 and perpendicular to the principal surface 201 of the base 101, X represents the shortest length of a portion (contact portion 301) where the shielding portion 109 and the light transmissive portion 108 are in contact with each other and Tg represents the thickness of the light transmissive portion 108. At this time, the following expression may be satisfied.

$$0.01 \le e^{-\mu_s X}/e^{-\mu_g Tg} \le 10 \quad (1)$$

Furthermore, the following expression may be satisfied.

$$0.05 \le e^{-\mu_s X}/e^{-\mu_g Tg} \le 2 \quad (2)$$

When expressions (1) and (2) are satisfied, the attenuation ratio of the scattered ray 154 passing through the shielding portion 109 becomes high, and it is possible to effectively suppress the scattered ray 154 passing through the shielding portion 109 to enter the sensor element 102. Note that contact (contact portion) here may include a portion where the surfaces are not in contact with each other within a surface roughness range except for points at which the surfaces are in contact with each other (a portion where the surfaces are not in contact with each other within the surface roughness range is also called a contact portion). The surface roughness may specifically be 20 μm or less, 10 μm or less, or 5 μm or less.

At this time, the scattered ray 154 may enter a portion close to the contact portion 301 of the light transmissive portion 108. Therefore, the following expression may be satisfied.

$$0.01 \le e^{-\mu_s X}/e^{-\mu_g Tg} \le 10 \quad (3)$$

Furthermore, the following expression may be satisfied.

$$0.05 \le e^{-\mu_s X}/e^{-\mu_g Tg} \le 2 \quad (4)$$

When expressions (3) and (4) are satisfied, it is possible to effectively suppress the scattered ray 154 entering the portion close to the contact portion 301 of the light transmissive portion 108.

As shown in FIG. 3B, the inner walls 202 of the shielding portion 109 and side walls of the light transmissive portion 108 may be in contact with each other. In this case, in the orthogonal projection with respect to the principal surface 201 of the base 101, contact portions 302 between the inner walls 202 of the shielding portion 109 and the side walls of the light transmissive portion 108 may surround the sensor element 102. That is, the light transmissive portion 108 may be arranged along the inner walls 202 of the shielding portion 109. In this example, μg represents the mass absorption coefficient of the light transmissive portion 108, μs represents the mass absorption coefficient of the shielding portion 109, and in a section passing through the sensor element 102 and perpendicular to the principal surface 201 of the base 101, Ws represents the shortest length between the outer wall and the inner wall 202 of the shielding portion 109 and Tg represents the thickness of the light transmissive portion 108. At this time, the following expression may be satisfied.

$$0.01 \le e^{-\mu_s X}/e^{-\mu_g Tg} \le 10 \quad (5)$$

Furthermore, the following expression may be satisfied.

$$0.05 \le e^{-\mu_s X}/e^{-\mu_g Tg} \le 2 \quad (6)$$

When expressions (5) and (6) are satisfied, the attenuation ratio of the scattered ray 154 passing through the shielding portion 109 becomes high, and it is possible to effectively suppress the scattered ray 154 passing through the shielding portion 109 to enter the sensor element 102, similar to the arrangement shown in FIG. 3A.

The arrangement shown in FIG. 3A is superior in assemblability when manufacturing the radiation detector 100. The arrangement shown in FIG. 3B is able to shield against the scattered ray 154 entering at an angle close to the direction along the principal surface 201 of the base 101 well. In each of the arrangements shown in FIGS. 3A and 3B, the width Ws of the shielding portion 109 can be, for example, about 2 mm to 3 mm. That is, in the arrangement shown in FIG. 3A, X can be about 2 mm to 3 mm. Furthermore, in the arrangement shown in FIG. 3A, a thickness Ts of the shielding portion 109 can be about 1 mm to 1.5 mm. If, for example, the thickness of the shielding portion 109 is 1.1 mm and the thickness of the sensor element 102 is 0.3 mm, a space of 0.8 mm is generated between the sensor element 102 and the opposite surface of the light transmissive portion 108. In the arrangement shown in FIG. 3B, the thickness of the shielding portion 109 may be about 5 mm, and the thickness of the light transmissive portion 108 may be about 4 mm.

The reflectance of the inner wall 202 of the shielding portion 109 with respect to the light generated by the scintillator 104 may be 20% or less. Furthermore, the reflectance of the inner wall 202 of the shielding portion 109 with respect to the light generated by the scintillator 104 may be 10% or less. The reflectance of the inner wall 202 of the shielding portion 109 with respect to light of a wavelength of 350 nm to 800 nm may be 20% or less, or 10% or less. By decreasing the light reflectance of the inner wall 202 of the shielding portion 109, it is possible to suppress stray light.

As shown in FIG. 3A, L represents a distance between the principal surface 201 of the base 101 and a surface of the lens portion 103 facing the principal surface 201, θ represents the aperture angle of the lens portion 103, and W represents a shortest distance between an optical axis 303 of the lens portion 103 and the inner wall 202 of the shielding portion 109 in the section passing through the sensor element 102 and perpendicular to the principal surface 201 of the base 101. At this time, the following expression may be satisfied.

$$0.6 \le W/(L \times \tan \theta) \le 5 \quad (7)$$

If the value is smaller than the lower limit of expression (7), the amount of light entering the sensor element decreases, and if the value is larger than the upper limit of expression (7), the overall detector increases in size. Note that the following expression may further be satisfied.

$$1.2 \le W/(L \times \tan \theta) \le 4 \quad (8)$$

The lower limit of expression (8) may be set to 1.5. This can suppress light having passed through the lens portion 103 from being reflected by the inner wall 202 of the shielding portion 109 to become stray light, and can decrease the amount of radiation entering the sensor element 102. In this example, L may represent an air conversion length (obtained by adding values each obtained by dividing an actual distance by a refractive index) from the facing surface (the surface closest to the base side) of the lens portion 103 to the principal surface 201 (or the light-receiving surface of the sensor element) of the base 101. That is, L is given by L=Σ(Lm/Nm) (Lm represents a physical distance and Nm represents the refractive index of a medium existing at the distance). Furthermore, the aperture angle of the lens portion 103 is an angle formed by the optical axis 303 and a light beam having a largest angle with respect to the optical axis 303 of the lens portion 103 among light beams that can be guided (imaged) by the lens portion.

As shown in FIG. 3A, the aperture angle θ is an angle at which light spreads from the optical axis. Referring to FIG. 3A, the optical axis 303 (sensor element 102) of the lens portion 103 is arranged at the center with respect to the left and right inner walls 202 of the shielding portion 109 but distances from the optical axis 303 (sensor element 102) to the left and right inner walls 202 may be different (for example, the sensor element 102 is offset from the center of the left and right inner walls 202). If the optical axis 303 (sensor element 102) of the lens portion 103 is offset from the center of the left and right inner walls 202, the distance W is the shortest distance between the optical axis 303 of the lens portion 103 and the inner wall 202 of the shielding portion 109, as described above, and is the distance between the optical axis 303 and the inner wall 202 close to the optical axis 303. Furthermore, if the sensor element 102 is the above-described linear sensor element, the distance W can be the shortest distance between the optical axis 303 of the lens portion 103 and the inner wall 202 of the shielding portion 109 in the widthwise direction (sub-scanning direction). In this case, the distance between the inner walls in the widthwise direction of the shielding portion 109 can be, for example, about 3 mm to 4 mm like 3.2 mm. For example, the sensor element 102 may have a width of 1 mm or less (≥0.4 mm), for example, 0.7 mm to 0.8 mm in the widthwise direction, and have a length of about 180 mm in the longitudinal direction.

If the lens portion 103 includes a plurality of lenses, the optical axis 303 of the lens portion 103 may be at the average position of the position coordinates of the optical axes of the respective lenses in a direction parallel to the principal surface 201 in the section perpendicular to the principal surface 201 of the base 101. Furthermore, if the lens portion 103 includes a plurality of lenses, the optical axis 303 of the lens portion 103 may be the central position between the optical axis of one lens and that of the other lens out of two lenses arranged at two ends in the direction parallel to the principal surface 201 among the lenses in the section perpendicular to the principal surface 201 of the base 101.

The structure of the base 101, the light transmissive portion 108, and the shielding portion 109 is not limited to those shown in FIGS. 3A and 3B. For example, in the structure shown in FIG. 3A, the outer wall of the light transmissive portion 108 and that of the shielding portion 109 may be flush with each other, or the outer wall of the shielding portion 109 may be arranged on the side of the sensor element 102 with respect to the outer wall of the light transmissive portion 108.

Figure 4A:
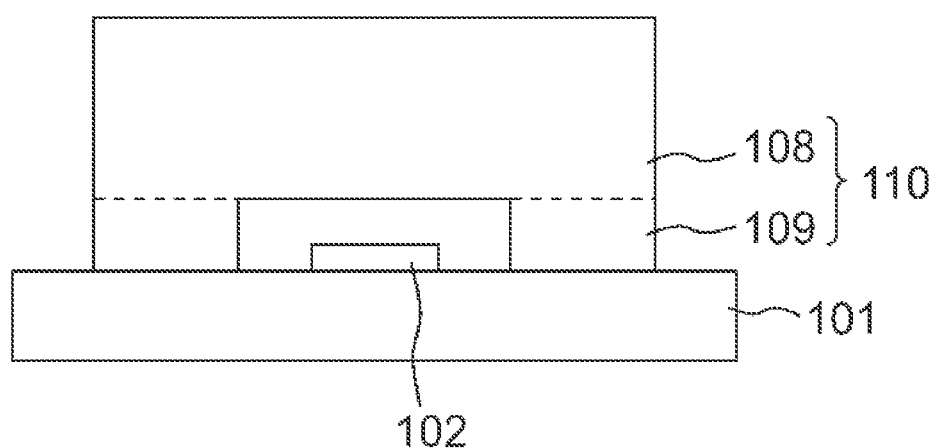
FIG. 4A is a sectional view showing a modification of the covering portion shown in FIG. 2.
Figure 4B:
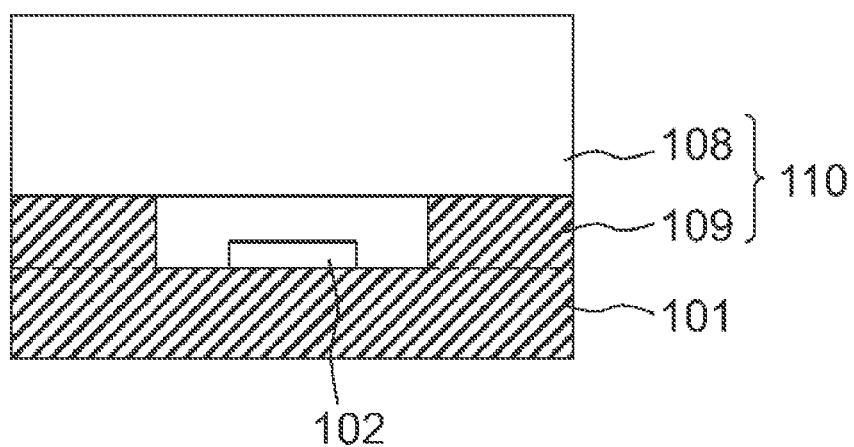
FIG. 4B is a sectional view showing a modification of the covering portion shown in FIG. 2.
Figure 4C:
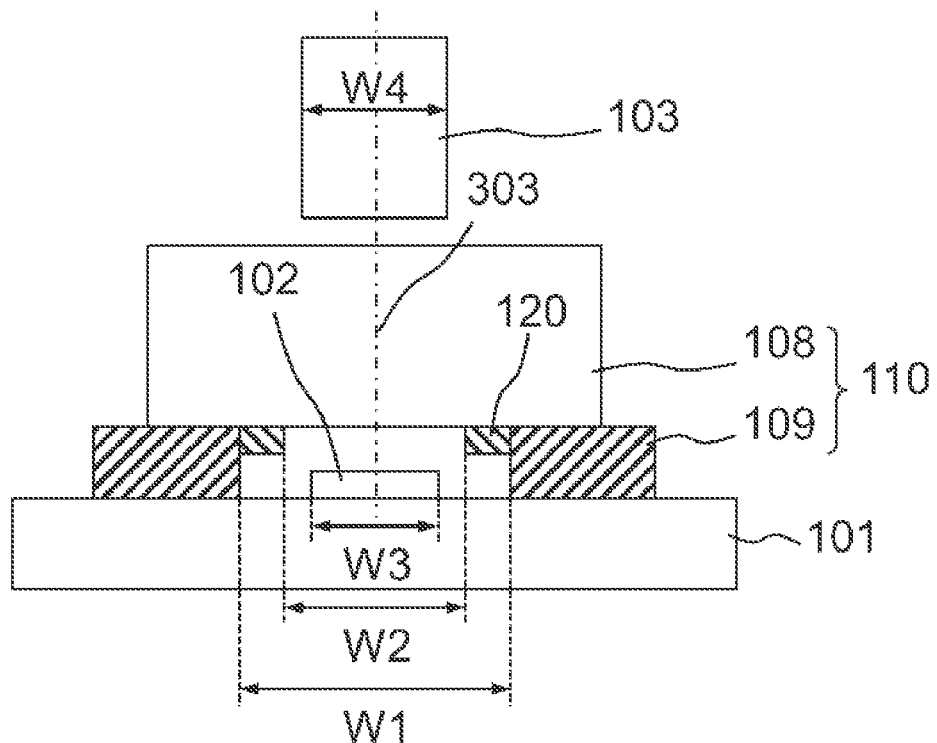
FIG. 4C is a sectional view showing a modification of the covering portion shown in FIG. 2.

As shown in FIG. 4A, the light transmissive portion 108 and the shielding portion 109 may be integrally made of the same material. As shown in FIG. 4B, the shielding portion 109 and the base 101 may be integrally made of the same material. As shown in FIG. 4C, a shielding member 120 that shields radiation (and may also shield light) may be provided between the inner walls facing each other of the shielding portion 109 (and between the light transmissive portion 108 and the base 101). In this case, the shielding member 120 may be integrally made of the same material as that of the shielding portion 109, or may be formed separately.

As shown in FIG. 4C, W1 represents the distance between the inner walls of the shielding portion 109, W2 represents the distance between the inner walls of the shielding member 120, W3 represents the width of the light-receiving element (effective light-receiving region) of the sensor element 102, and W4 represents the width of the lens portion 103 (effective lens portion). At this time, at least one of the following expressions may be satisfied.

$$W1/W2>1 \quad (9)$$

$$W4>W2>W3 \quad (10)$$

$$W4<W2<W3 \quad (11)$$

The distance W1 indicates the distance between the inner walls of the shielding portion having a function of shielding radiation at a position closest to the base 101 out of a position at which the sensor element 102 is arranged and a position at which the shielding portion 109 is arranged. The distance W2 indicates the shortest distance among the distances between the inner walls of the shielding portion having a function of shielding radiation at a position on the side of the base 101 with respect to the light transmissive portion 108. Alternatively, the distance W2 may indicate the distance between the inner walls of the shielding portion which has a function of shielding radiation and is arranged on the surface of the light transmissive portion 108 on the side of the base 101.

If expression (9) is satisfied, it is possible to reduce the dose of radiation entering the sensor element 102 and also prevent the incidence of stray light. Expression (9) preferably satisfies:

$$2>W1/W2>1.1 \quad (9a)$$

Expressions (10) and (11) are effective conditional expressions to keep the balance between ensuring of the amount of light from the lens portion 103 to the sensor element 102 and the decrease of the incident amount of radiation on the sensor element 102. In expressions (10) and (11), the relationship among W4, W2, and W3 may reverse depending on the relationship between the width W3 of the light-receiving element of the sensor element 102 and the width W4 of the lens portion 103. Expressions (10) and (11) preferably satisfy one of:

$$W4\times0.9>W2>W3\times1.1 \quad (10a)$$

$$W4\times1.1<W2<W3\times0.9 \quad (11a)$$

Referring to FIG. 4C, the shielding member 120 protrudes stepwise with respect to the shielding portion 109. The present invention is not limited to this, and the shielding member 120 may be tapered. As described above, the shielding portion 109 and the shielding member 120 may be formed integrally, as a matter of course.

Figure 4D:
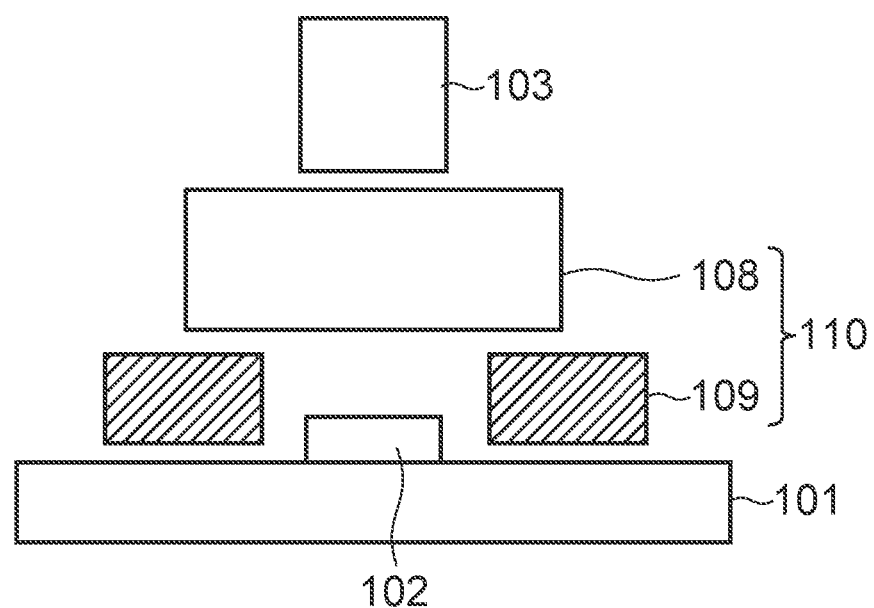
FIG. 4D is a sectional view showing a modification of the covering portion shown in FIG. 2.

The shielding portion 109 and the light transmissive portion 108 need not be in tight contact with each other and the shielding portion 109 and base 101 need not be in tight contact with each other. As shown in FIG. 4D, there may be a gap between the shielding portion 109 and the light transmissive portion 108, and a gap between the shielding portion 109 and the base 101 on which the sensor element 102 is arranged. For example, there may be a space between the shielding portion 109 and the light transmissive portion 108, and the shielding portion 109 and the base 101 may be in tight contact with each other. Alternatively, for example, there may be a space between the shielding portion 109 and the base 101, and the shielding portion 109 and the light transmissive portion 108 may be in tight contact with each other. When the covering portion 110 including the shielding portion 109 and the light transmissive portion 108 is arranged, it is possible to suppress the influence of the scattered ray 154 or the like. A joint member (for example, an adhesive, a double-sided adhesive tape, or the like) for joining the shielding portion 109 and the light transmissive portion 108 or the shielding portion 109 and the base 101 may be arranged between them.

In this embodiment, in addition to the light transmissive portion 108, the shielding portion 109 is arranged between the light transmissive portion 108 and the principal surface 201 of the base 101 so that the inner walls 202 of the shielding portion 109 are located on the periphery of the sensor element 102. This can effectively suppress the scattered ray 154 entering at an angle close to the direction along the principal surface 210 of the base 101.

Figure 5:
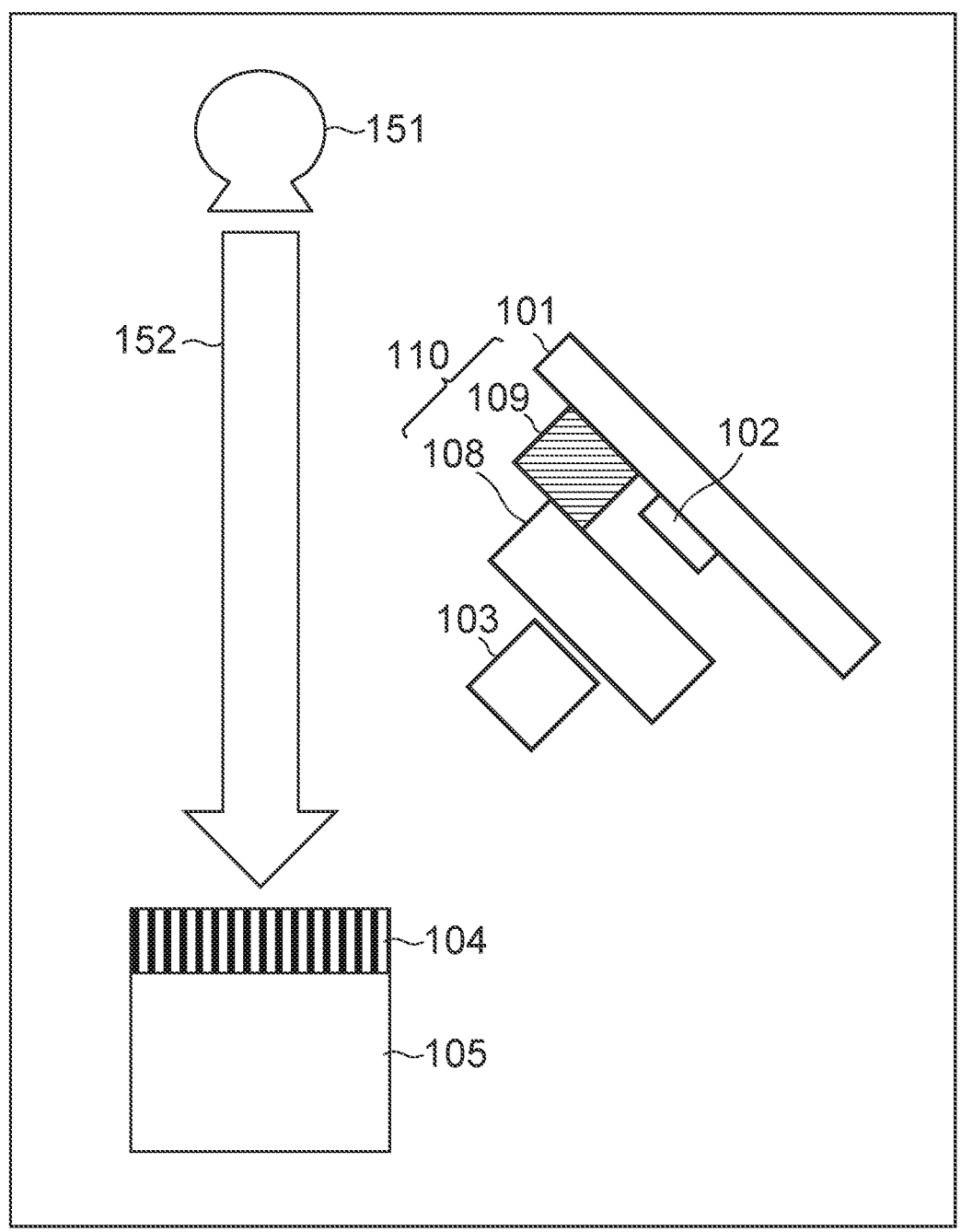
FIG. 5 is a view showing a modification of the arrangement of the covering portion shown in FIG. 2.

FIGS. 2 to 4D show the examples in each of which the shielding portion 109 is arranged to surround the whole periphery of the sensor element 102 provided on the base 101. The present invention, however, is not limited to them. As described above, when the inner walls 202 of the shielding portion 109 are arranged on at least part of the periphery of the sensor element 102, it is possible to suppress the scattered ray 154 entering the sensor element 102 at an angle close to the direction along the principal surface 201 of the base 101. More specifically, as shown in FIG. 5, the shielding portion 109 may be arranged along a side of the sensor element 102 closest to the radiation source 151. Alternatively, for example, the shielding portion 109 may be arranged along three sides of the sensor element 102 except for a side farthest from the radiation source 151. As described above, the shielding portion 109 is arranged to suppress the incidence of the scattered ray 154 on the sensor element 102. However, as shown in FIG. 1, even if the housing 107 is arranged on the periphery of the covering portion 110 including the shielding portion 109 and the light transmissive portion 108, the radiation 152 may enter from the side of the radiation source 151. Therefore, by arranging the shielding portion 109 between the sensor element 102 and the radiation source 151, it is possible to suppress the influence of the radiation 152 that directly enters from the radiation source 151.

Figure 6A:
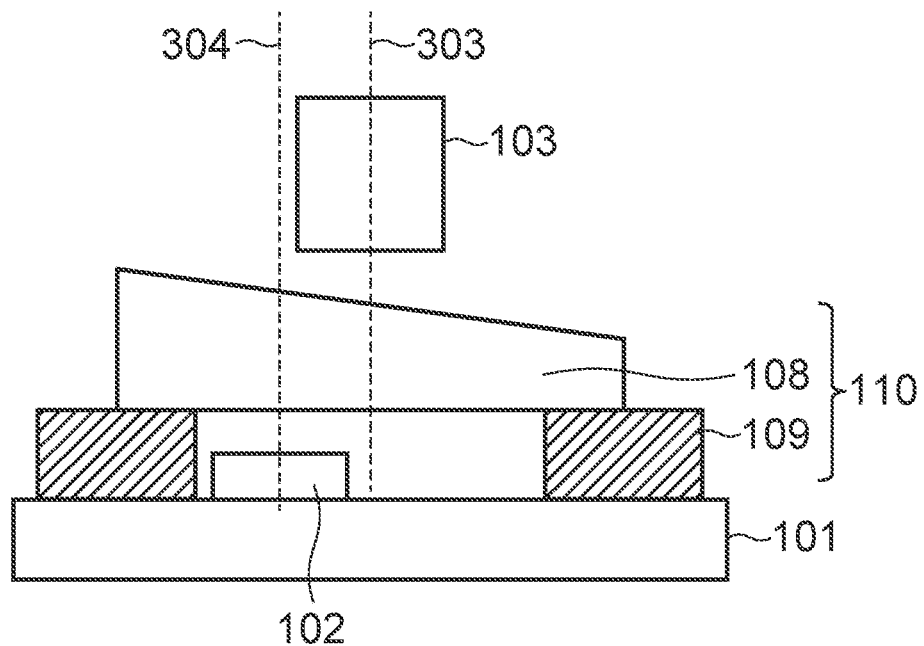
FIG. 6A is a sectional view showing a modification of the covering portion shown in FIG. 2.
Figure 6B:
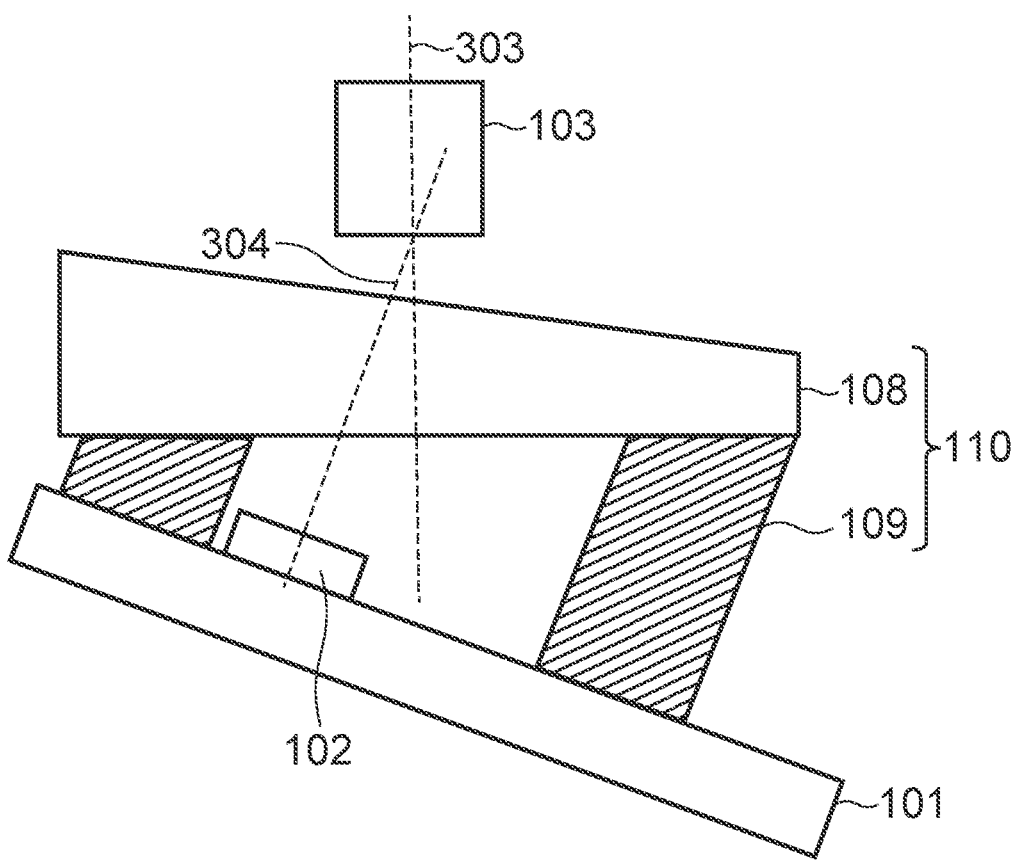
FIG. 6B is a sectional view showing a modification of the covering portion shown in FIG. 2.
Figure 6C:
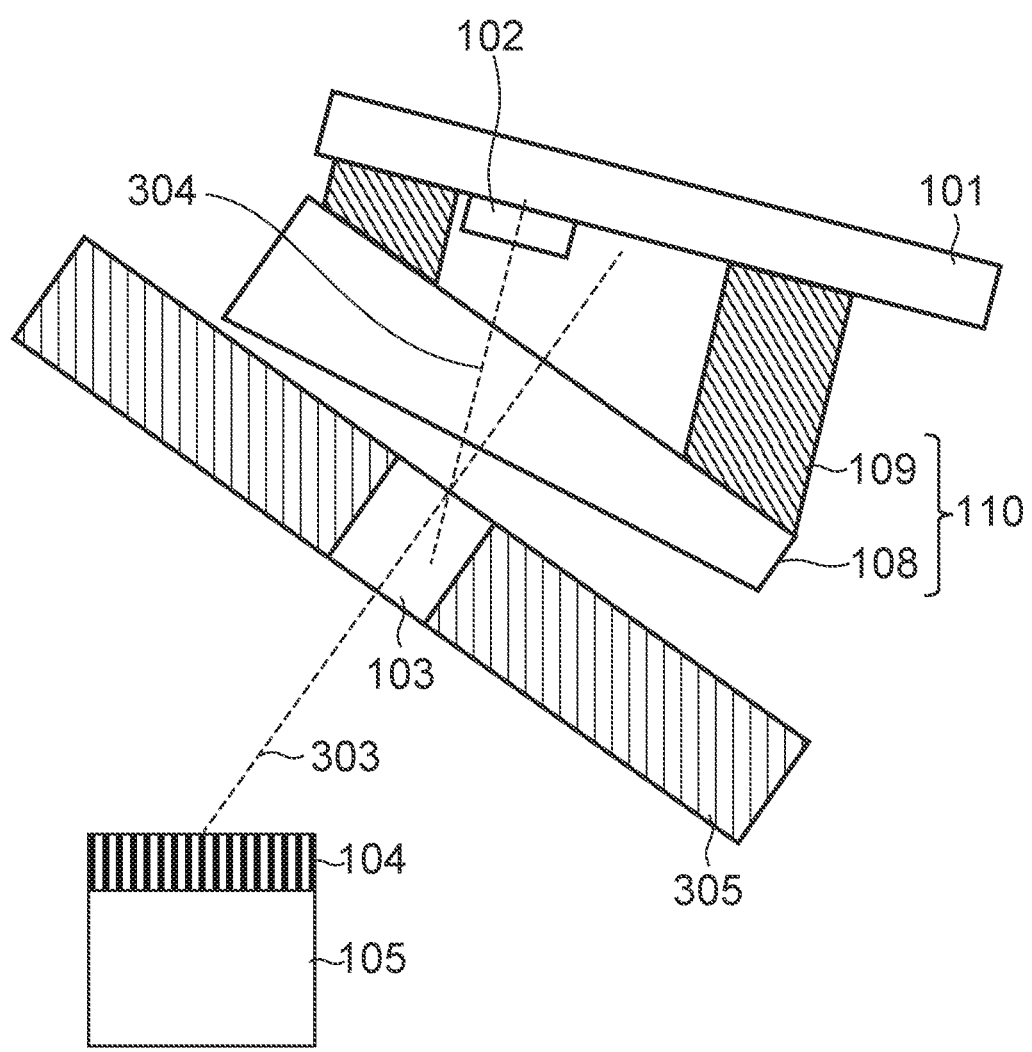
FIG. 6C is a sectional view showing a modification of the arrangement of the covering portion shown in FIG. 2.

The above-described embodiment has explained the arrangement in which the optical axis 303 (a light beam passing the optical axis 303) of the lens portion 103 is perpendicular to the incident surface and exit surface of the light transmissive portion 108 and parallel to the normal of the incident surface of the sensor element 102. The present invention, however, is not limited to this. For example, as shown in FIG. 6A, the incident surface of the light transmissive portion 108 may tilt with respect to the optical axis 303 of the lens portion 103. As shown in FIG. 6B, the normals of the incident surface of the light transmissive portion 108 and the incident surface of the sensor element 102 may tilt with respect to the optical axis 303. Furthermore, as shown in FIG. 6C, all the normals of the incident surface and exit surface of the light transmissive portion 108 and the incident surface of the sensor element 102 may tilt with respect to the optical axis. At this time, light having entered the light transmissive portion 108 from the lens portion 103 is refracted in accordance with the tilts of the incident surface and exit surface of the light transmissive portion 108. That is, the light transmissive portion 108 may have an effect of bending light having passed through the lens portion 103 from the optical axis 303 of the lens portion 103. In other words, the light transmissive portion 108 may be configured to change (deflect, refract, bend, or translate), from the optical axis, the optical path of a light beam, having passed through the optical axis of the lens portion 103, of the light (light whose wavelength has been converted) generated by the scintillator 104. For example, in the arrangement shown in FIG. 6A, the light beam having passed through the optical axis is refracted to the left side of FIG. 6A with respect to the optical axis 303 of the lens portion 103 by the light transmissive portion 108, and enters the sensor element 102 arranged on the left side of the optical axis 303 of the lens portion 103. That is, the optical axis 303 of the lens portion 103 need not overlap a normal 304 at the center of the light incident surface of the sensor element 102. For example, as shown in FIG. 6A, the optical axis 303 of the lens portion 103 need not overlap the sensor element 102. In other words, the sensor element 102 may be arranged at a position not overlapping the optical axis 303 of the lens portion 103. For example, in the orthogonal projection with respect to the principal surface 201 of the base 101 on which the sensor element 102 is arranged, the lens portion 103 and the sensor element 102 may be arranged at positions not overlapping each other. That is, in the orthogonal projection with respect to the principal surface 201 of the base 101 on which the sensor element 102 is arranged, the lens portion 103 and the sensor element 102 may be arranged at positions shifted from each other in the widthwise direction.

As shown in FIG. 6B, the normal 304 at the center of the light incident surface of the sensor element 102 may tilt with respect to the optical axis 303 of the lens portion 103. In this case, as shown in FIG. 6B, the height of the shielding portion 109 (the length between the light transmissive portion 108 and the base 101) may be different depending on a location. In this case as well, as shown in FIG. 6B, the optical axis 303 of the lens portion 103 need not overlap the sensor element 102. That is, the sensor element 102 may be arranged at a position not overlapping the optical axis 303 of the lens portion 103. Note that the optical axis 303 indicates the optical axis of the lens portion 103 and its extension.

As shown in FIG. 6C, the lens portion 103 is fixed to the housing 107 (see FIG. 1) via a lens fixing portion 350, and can thus be positioned in the housing 107. As shown in FIG. 6C, the lens fixing portion 350 is arranged to contact the side surfaces of the lens portion 103 and cover the light transmissive portion 108. At this time, if, for example, the lens fixing portion 350 is made of a metal such as lead or tungsten, the lens portion 103 may transmit radiation more easily than the lens fixing portion 350. That is, the radiation absorptance of the lens fixing portion 350 may be higher than that of the lens portion 103. By arranging the sensor element 102 at a position not overlapping the optical axis 303 of the lens portion 103, it is possible to suppress the scattered ray 154 having passed through the lens portion 103 from entering the sensor element 102.

The intensity of the scattered ray 154 that enters the scintillator 104 to be scattered is lower as the angle with respect to the surface of the scintillator 104 is smaller. Therefore, for example, if the light transmissive portion 108 bends the light in the direction opposite to that shown in FIG. 6C and the sensor element 102 is arranged on the lower right side of FIG. 6C, the influence of the scattered ray 154 can be suppressed, as compared with a case in which the sensor element 102 is arranged in front of the optical axis 303 of the lens portion 103. In this arrangement, even if the lens fixing portion 350 absorbs radiation less than the lens portion 103, it is possible to obtain the effect of suppressing the influence of the scattered ray 154.

Consider the base 101 on which the sensor element 102 is arranged. As described above, as the base 101, a circuit board (printed circuit board) on which one or a plurality of wiring layers (wiring patterns) are formed may be used. As described above, by arranging the covering portion 110 including the shielding portion 109 and the light transmissive portion 108, the incidence of the scattered ray 154 on the sensor element 102 is suppressed. However, it is difficult to completely prevent the incidence of the radiation. Furthermore, radiation may enter a portion of the circuit board (base 101) which is not covered with the covering portion 110. If radiation enters the circuit board, backscattering such that radiation is reflected in the wiring layer arranged in the circuit board or the like may occur. If backscattering occurs, an integrated circuit including a semiconductor element (for example, the sensor element 102) mounted on the circuit board may be damaged by backscattered radiation.

Figure 7A:
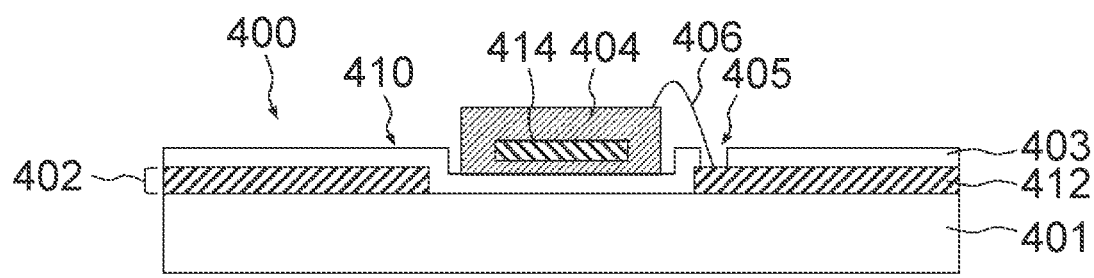
FIG. 7A is a sectional view showing an example of the arrangement of a circuit board according to the embodiment.

FIG. 7A is a sectional view showing an example of the arrangement of a circuit board 400 according to this embodiment. The circuit board 400 includes a mounting surface 410 on which a semiconductor package 404 containing an integrated circuit (a semiconductor chip such as a CMOS sensor) including a light-receiving element (a photodiode or the like) and a semiconductor element (a transistor or the like) is mounted. The circuit board 400 and the semiconductor package 404 can correspond to the above-described base 101 and sensor element 102, respectively. This circuit board 400 includes at least one wiring layer 402 formed by a conductor containing copper (another metal may be possible). The semiconductor package includes the integrated circuit and an exterior member containing the integrated circuit, but the present invention is not limited to this. The semiconductor package described in this embodiment may be considered as an integrated circuit. Furthermore, the semiconductor package need not always seal the integrated circuit (or semiconductor element).

The circuit board 400 includes a core layer 401 in which the wiring layer 402 is formed. The circuit board 400 may also include an insulating layer 403 (resist layer) covering the wiring layer 402. In the arrangement shown in FIG. 7A, the semiconductor package 404 including an integrated circuit 414 is arranged on the core layer 401 via the insulating layer 403. However, the present invention is not limited to this, and the semiconductor package 404 may be arranged directly on the core layer 401. In the wiring layer 402, a conductor 412 forming the wiring pattern is arranged. The conductor 412 forming the wiring pattern and the integrated circuit 414 mounted on the semiconductor package 404 can be electrically connected via a lead wire 406 and a portion of the conductor 412 exposed to an opening 405 formed in the insulating layer 403. A conductive member made of a metal or the like may be buried in the opening 405. In this case, the conductor 412 and the integrated circuit 414 mounted on the semiconductor package 404 are electrically connected via the lead wire 406 and the conductive member buried in the opening 405. In an orthogonal projection with respect to the mounting surface 410, the wiring layer 402 is a wiring layer in which the ratio of the area of a portion, where the conductor 412 forming the wiring pattern is arranged, with respect to a region overlapping the integrated circuit 414 contained in the semiconductor package 404 is 20% or less. In the orthogonal projection with respect to the mounting surface 410, the wiring layer 402 may be a wiring layer in which the ratio of the area of the portion, where the conductor 412 is arranged, with respect to the region overlapping the integrated circuit 414 is 1% or less. Furthermore, as shown in FIG. 7A, in the orthogonal projection with respect to the mounting surface 410, the wiring layer 402 may be a wiring layer in which the conductor 412 forming the wiring pattern is not arranged in the region overlapping the integrated circuit 414. The wiring layer 402 can be regarded as a wiring layer in which the ratio of the portion, where the conductor 412 forming the wiring pattern is arranged, with respect to the region overlapping the integrated circuit 414 is low.

Figure 7B:
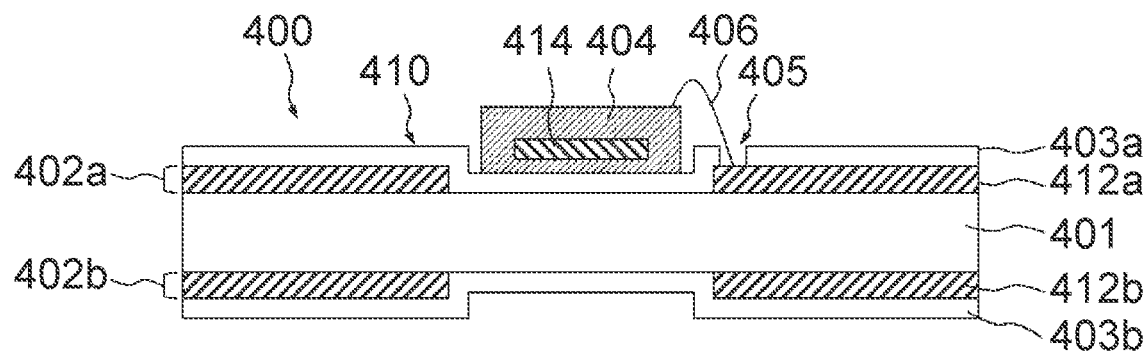
FIG. 7B is a sectional view showing an example of the arrangement of the circuit board according to the embodiment.

The number of wiring layers 402 arranged in the circuit board 400 is not limited to one. For example, as shown in FIG. 7B, two wiring layers may be arranged in the circuit board 400. In the arrangement shown in FIG. 7B, in an orthogonal projection with respect to the mounting surface 410, the two wiring layers arranged in the circuit board 400 are wiring layers 402*a* and 402*b* in each of which the ratio of a portion, where a conductor 412*a* or 412*b* forming a wiring pattern is arranged, with respect to the region overlapping the integrated circuit 414 is low.

The effect of the fact that in the circuit board 400, the ratio of the portion, where the conductor 412 forming the wiring pattern is arranged, with respect to the region overlapping the integrated circuit 414 is low will be described next with reference to FIGS. 8A and 8B. The circuit board 400 may be used in an environment where a radiation detector or the like is exposed to radiation. This is, for example, a case in which the integrated circuit 414 including a photoelectric conversion portion such as a light-receiving element is mounted on the semiconductor package 404 mounted on the circuit board 400 to generate a radiation image. In this example, assume that a scintillator that converts radiation into light and the integrated circuit 414 including the photoelectric conversion portion that converts the light converted by the scintillator into an electrical signal are mounted on the semiconductor package 404. For the sake of descriptive simplicity, assume that the integrated circuit 414 including the photoelectric conversion portion is irradiated with radiation 501 having passed through a subject, thereby generating a radiation image.

A circuit board 500 according to a comparative example shown in FIG. 8B will first be described. The circuit board 500 includes a wiring layer 422*a* including a wiring pattern formed by a conductor 432*a*, and a wiring layer 422*b* including a wiring pattern formed by a conductor 432*b*. In an orthogonal projection with respect to a mounting surface 410 on which a semiconductor package 404 is mounted, the two wiring layers are wiring layers in each of which the ratio of the area of a portion, where the conductor 432*a* or 432*b* is arranged, with respect to a region overlapping an integrated circuit 414 in the semiconductor package 404 exceeds 20%.

Radiation 501 is converted into light by a scintillator mounted on the semiconductor package 404, and used to generate a radiation image. However, part of the incident radiation 501 enters the circuit board 500 without being absorbed (converted) by the scintillator mounted on the semiconductor package 404. Part of the radiation 501 having passed through the semiconductor package 404 passes the circuit board 500. However, the remaining part of the radiation 501 is backscattered in the conductors 432*a* and 432*b* forming the wiring patterns of the wiring layers 422*a* and 422*b*, and reenters the semiconductor package 404 as a scattered ray. This is because the conductors 432*a* and 432*b* contain a metal and scatter/reflect radiation more easily than the core layer 401 of the circuit board 400 or 500. A wiring pattern containing gold, silver, or copper has a high degree of scattering of radiation, as compared with a wiring pattern containing aluminum or the like. In general, copper or a copper alloy is often used for a conductor forming a wiring pattern used for a circuit board, and the radiation 501 entering the circuit board 500 is highly probably backscattered.

If the scattered ray enters, due to backscattering, the integrated circuit 414 mounted on the semiconductor package 404, the photoelectric conversion portion of the integrated circuit 414 may erroneously detect the scattered ray. In general, if radiation enters the light-receiving element of the integrated circuit 414 mounted on the semiconductor package 404, this may cause damage such that, for example, bonding of silicon crystal or the like is separated to generate a dangling bond. Generation of a dangling bond may cause a white spot or the like. Damage caused by radiation irradiation may cause an operation failure of the integrated circuit 414 such as a semiconductor element in addition to the light-receiving element. To suppress the dose of radiation entering the integrated circuit 414 mounted on the semiconductor package 404, a structure for suppressing scattering/reflection of radiation incident on the circuit board is required.

Figure 8A:
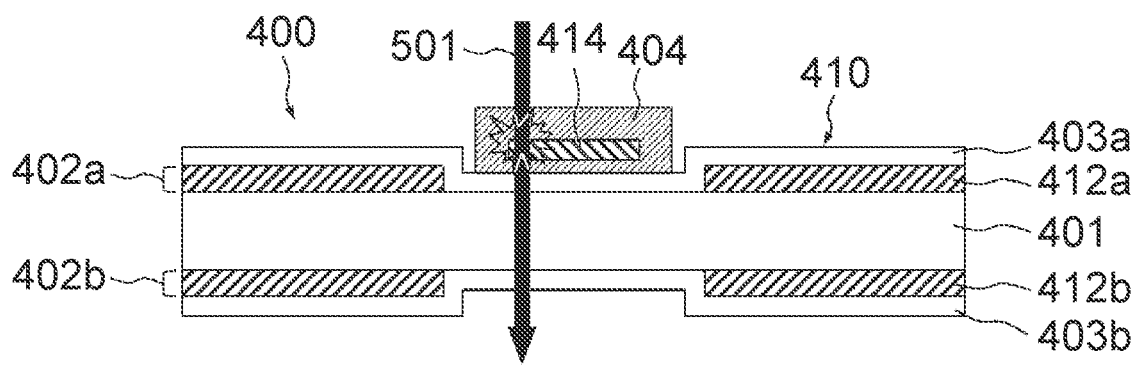
FIG. 8A is a sectional view for explaining the effect of the circuit board according to the embodiment.
Figure 8B:
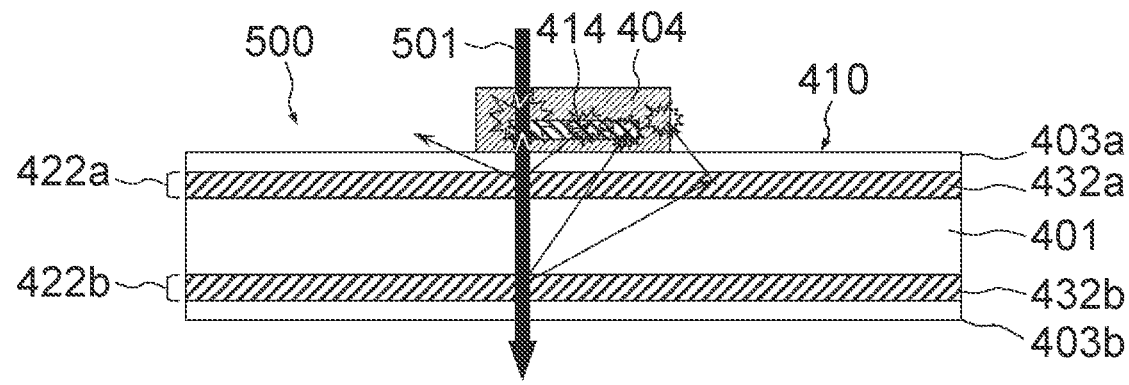
FIG. 8B is a sectional view showing a circuit board of a comparative example for explaining the effect of the circuit board according to the embodiment.

To cope with this, as shown in FIG. 8A, in the circuit board 400 according to this embodiment, the wiring layer 402 in which the ratio of a portion, where the conductor 412 forming the wiring pattern is arranged, with respect to the region overlapping the integrated circuit 414 included in the semiconductor package 404 is as low as 20% or less in the orthogonal projection with respect to the mounting surface 410 is arranged. This can suppress backscattering of radiation in the conductor 412 arranged in the circuit board 400, as compared with the arrangement shown in FIG. 8B in which a large portion of the conductor 432a or 432b is arranged in the region overlapping the integrated circuit 414, thereby suppressing damage to the integrated circuit 414 mounted on the semiconductor package 404. As a result of examination by the inventor, it was found that the possibility of the incidence of backscattered radiation on the integrated circuit 414 became high when the ratio of the portion, where the conductor 412 is arranged, with respect to the region overlapping the integrated circuit 414 included in the semiconductor package 404 exceeded 20%. Therefore, by setting, to 20% or less, the ratio of the portion, where the conductor 412 is arranged, with respect to the region overlapping the integrated circuit 414, it is possible to suppress damage to the integrated circuit 414. In the wiring layer 402, the conductor 412 forming the wiring pattern is arranged in a portion whose ratio with respect to the region overlapping the integrated circuit 414 is 20% or less in the orthogonal projection with respect to the mounting surface 410. This can interconnect, for example, the right and left wiring patterns in the wiring layer 402a shown in FIG. 8A using the wiring pattern passing through the region overlapping the semiconductor package 404, thereby suppressing a decrease in the degree of freedom when designing the wiring patterns.

Figure 7C:
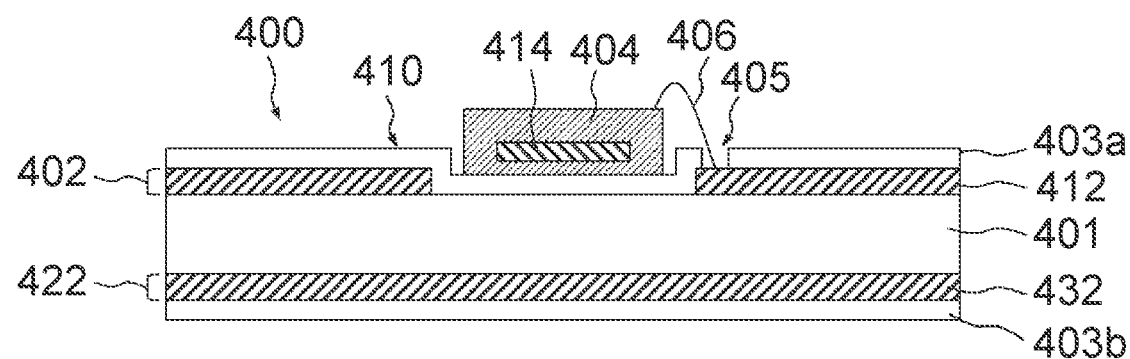
FIG. 7C is a sectional view showing an example of the arrangement of the circuit board according to the embodiment.

A modification of the circuit board 400 according to this embodiment will be described with reference to FIGS. 7C to 7E. The circuit board 400 shown in FIG. 7C includes two wiring layers. In the orthogonal projection with respect to the mounting surface 410, one of the two wiring layers is the wiring layer 402 in which the ratio of the portion, where the conductor 412 is arranged, with respect to the region overlapping the integrated circuit 414 included in the semiconductor package 404 is low, and the other wiring layer is a wiring layer 422 in which a large portion of the conductor 432 is arranged in the region overlapping the integrated circuit 414. When a plurality of wiring layers are arranged in the circuit board 400, at least one wiring layer is the wiring layer 402 in which the ratio of a portion of the conductor 412 arranged in the region overlapping the integrated circuit 414 included in the semiconductor package 404 is low. This can suppress backscattering of radiation in the circuit board 400, as compared with a case in which all the wiring layers are the wiring layers 422 in each of which a large portion of the conductor 432 is arranged in the region overlapping the integrated circuit 414, like the circuit board 500 shown in FIG. 8B. If both the wiring layers 402 and 422 are arranged as wiring layers in the circuit board 400, the wiring layer, among the wiring layers, arranged closest to the mounting surface 410 may be the wiring layer 402, as shown in FIG. 7C. This is because radiation scattered/reflected in the wiring layer closer to the integrated circuit 414 included in the semiconductor package 404 highly probably reenters the semiconductor package 404, as compared with radiation scattered/reflected in the wiring layer away from the integrated circuit 414.

Figure 7D:
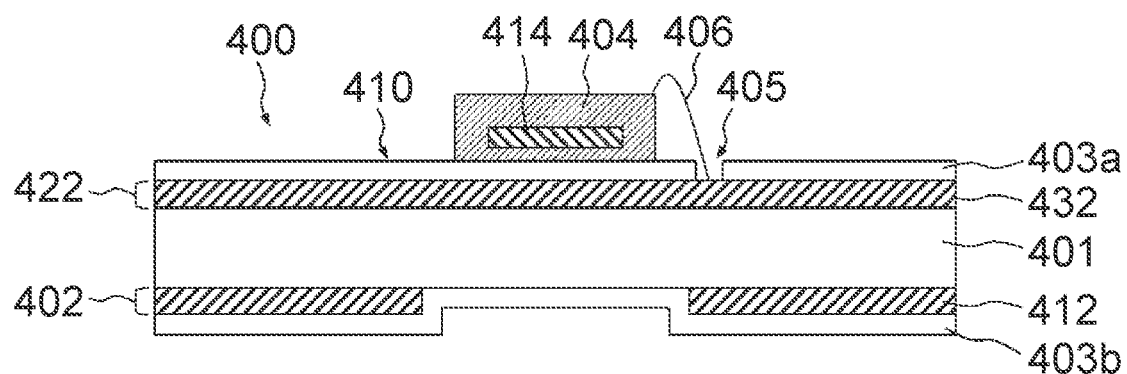
FIG. 7D is a sectional view showing an example of the arrangement of the circuit board according to the embodiment.
Figure 7E:
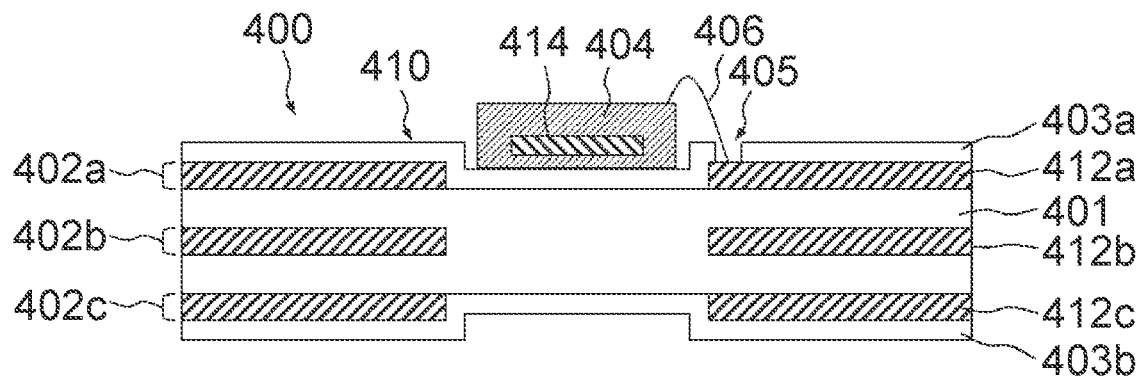
FIG. 7E is a sectional view showing an example of the arrangement of the circuit board according to the embodiment.

As shown in FIG. 7D, the wiring layer 422 may be arranged close to the mounting surface 410. In other words, the wiring layer 422 in which a large portion of the conductor 432 is arranged in the region overlapping the integrated circuit 414 included in the semiconductor package 404 may be arranged between the semiconductor package 404 and the wiring layer 402 in which a small portion of the conductor 412 is arranged in the region overlapping the integrated circuit 414. In this case as well, it is possible to suppress backscattering of radiation in the circuit board 400, as compared with a case in which all the wiring layers are the wiring layers 422 in each of which a large portion of the conductor 432 is arranged in the region overlapping the integrated circuit 414.

Furthermore, the number of wiring layers arranged in the circuit board 400 may be three or more. In this case, as shown in FIG. 7E, all the wiring layers arranged in the circuit board 400 may be the wiring layers 402 in each of which the ratio of a portion, where the conductor 412 is arranged, with respect to the region overlapping the integrated circuit 414 included in the semiconductor package 404 is low. Alternatively, the wiring layers 402 and 422 may be arranged in combination.

Figure 9A:
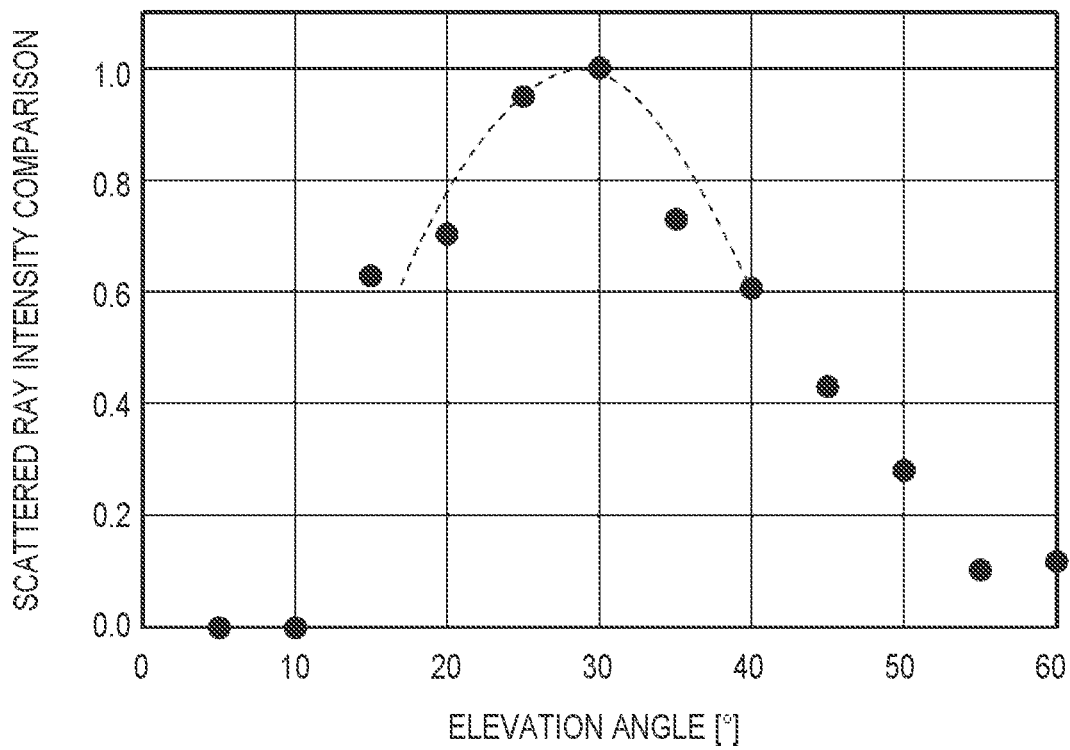
FIG. 9A is a graph showing the angle dependency of a scattered ray.
Figure 9B:
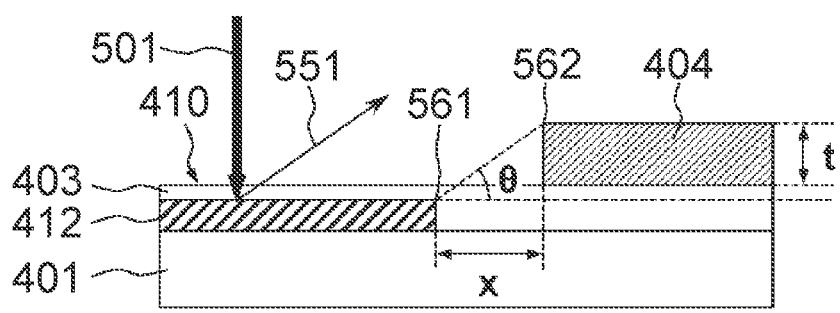
FIG. 9B is a sectional view for explaining the angle dependency of the scattered ray.

Details of the region where the conductor 412 forming the wiring pattern is arranged in the wiring layer 402 will be described next with reference to FIGS. 9A to 9C. This example assumes a circuit board on which the conductor 412 forming a wiring pattern is not arranged in the region overlapping the integrated circuit 414 included in the semiconductor package 404 in the orthogonal projection with respect to the mounting surface 410. That is, the arrangement of the wiring pattern that can suppress the influence of backscattering on the semiconductor package 404 more will be described. FIG. 9A shows the angle dependency of the scattered ray intensity. This indicates the ratio of the intensity at each angle of a scattered ray 551 when the radiation 501 is emitted from the normal direction of the conductor 412, as shown in FIG. 9B, a plane along the surface of the conductor 412 is set at 0°, and the normal direction is set at 90°. It is understood that as the angle is larger, the scattered ray intensity is higher, and the scattered ray intensity reaches the peak around 30°. Among others, it is understood that the scattered ray intensity is relatively high at an angle of 25° to 30°. At an angle of 15° or less, the scattered ray intensity abruptly decreases. FIG. 9C is a table summarizing the numerical values in FIG. 9A.

Thus, the conductor 412 forming the wiring pattern may be arranged so that the maximum angle of an elevation angle θ of a straight line connecting the semiconductor package 404 and the conductor 412 forming the wiring pattern arranged in the wiring layer 402 with respect to a plane on which the wiring layer 402 is arranged is 30° or less (or 25° or less). For example, a portion, closest to the semiconductor package 404, of the conductor 412 forming the wiring pattern is set as a portion 561. An upper end of a portion, closest to the portion 561, of the semiconductor package 404 is set as a portion 562. In this case, the conductor 412 and the semiconductor package 404 are arranged so that the elevation angle θ from the portion 561 to the portion 562 with reference to the surface of the conductor 412 is 25° or less. This can suppress the influence of the scattered ray 551. By setting the elevation angle θ to 15° or less, the scattered ray 551 hardly enters the semiconductor package 404. This can further suppress the influence of the scattered ray 551 on the integrated circuit 414 mounted on the semiconductor package 404.

It is more essential to suppress the influence of the scattered ray 551 on the integrated circuit 414 (semiconductor chip) mounted on the semiconductor package 404. Therefore, the maximum angle of the elevation angle of the straight line connecting the integrated circuit 414 mounted on the semiconductor package 404 and the conductor 412 forming the wiring pattern arranged in the wiring layer 402 with respect to the plane on which the wiring layer 402 is arranged is preferably 30° or less. More specifically, the conductor 412 forming the wiring pattern may be arranged so that the maximum angle is 25° or less (or 15° or less). Furthermore, the area of a portion of the conductor 412 forming the wiring pattern, for which the maximum angle of the elevation angle of the straight line connecting the conductor 412 and the integrated circuit 414 with respect to the plane is 30° or less (25° or less or 15° or less), is 80% or more of the area of the overall conductor. A numerical value of 80% may be replaced by 95% or more.

Consider a case in which the thickness of the semiconductor package 404 is about 250 µm to 350 µm. In this case, if the semiconductor package 404 and the conductor 412 forming the wiring pattern arranged in the wiring layer 402 are separated by 1 mm or more in the orthogonal projection with respect to the mounting surface 410, the above-described elevation angle θ is 25° or less. This can suppress the influence of the scattered ray 551 on the semiconductor chip mounted on the semiconductor package 404. Furthermore, if the semiconductor package 404 and the conductor 412 forming the wiring pattern arranged in the wiring layer 402 are separated by 1.5 mm or more in the orthogonal projection with respect to the mounting surface 410, the elevation angle θ is 15° or less, thereby making it possible to further suppress the influence of the scattered ray 551.

As described above, it is more essential to suppress the influence of the scattered ray 551 on the integrated circuit 414 (semiconductor chip) mounted on the semiconductor package 404. Therefore, in the orthogonal projection with respect to the mounting surface 410, the conductor 412 forming the wiring pattern arranged in the wiring layer 402 and the integrated circuit 414 mounted on the semiconductor package 404 may be separated by 1 mm or more. Furthermore, in the orthogonal projection with respect to the mounting surface 410, the conductor 412 forming the wiring pattern arranged in the wiring layer 402 and the integrated circuit 414 mounted on the semiconductor package 404 may be separated by 1.5 mm or more.

As an application of the circuit board 400 according to this embodiment, a radiation detector using the circuit board 400, a radiation detection apparatus, and an inspection apparatus will be described next with reference to FIG. 10.

A radiation detector 700 includes a scintillator 702 that receives radiation and emits light whose wavelength is different from that of the radiation, the above-described circuit board 400, and the semiconductor package 404 that is mounted on the mounting surface 410 of the circuit board 400 and includes the integrated circuit 414 including a light-receiving element 701 for receiving the light emitted by the scintillator 702. At this time, on the circuit board 400, a semiconductor package on which another integrated circuit such as a semiconductor element for operating the light-receiving element 701 is mounted in addition to the integrated circuit 414 including the light-receiving element 701 may be mounted.

Furthermore, the radiation detector 700 may form a radiation detection apparatus 710 together with a radiation source 704. The radiation detection apparatus 710 generates a radiation image of an object 705 arranged between the radiation source 704 and the radiation detector 700. For example, an image generation processor 706 generates a radiation image based on a signal acquired by the light-receiving element 701. As shown in FIG. 10, the image generation processor 706 may be mounted on the semiconductor package mounted on the circuit board 400. The image generation processor 706 may be implemented on an external computer of the circuit board 400 to which the signal acquired by the light-receiving element 701 is transmitted from the circuit board 400.

Figure 10:
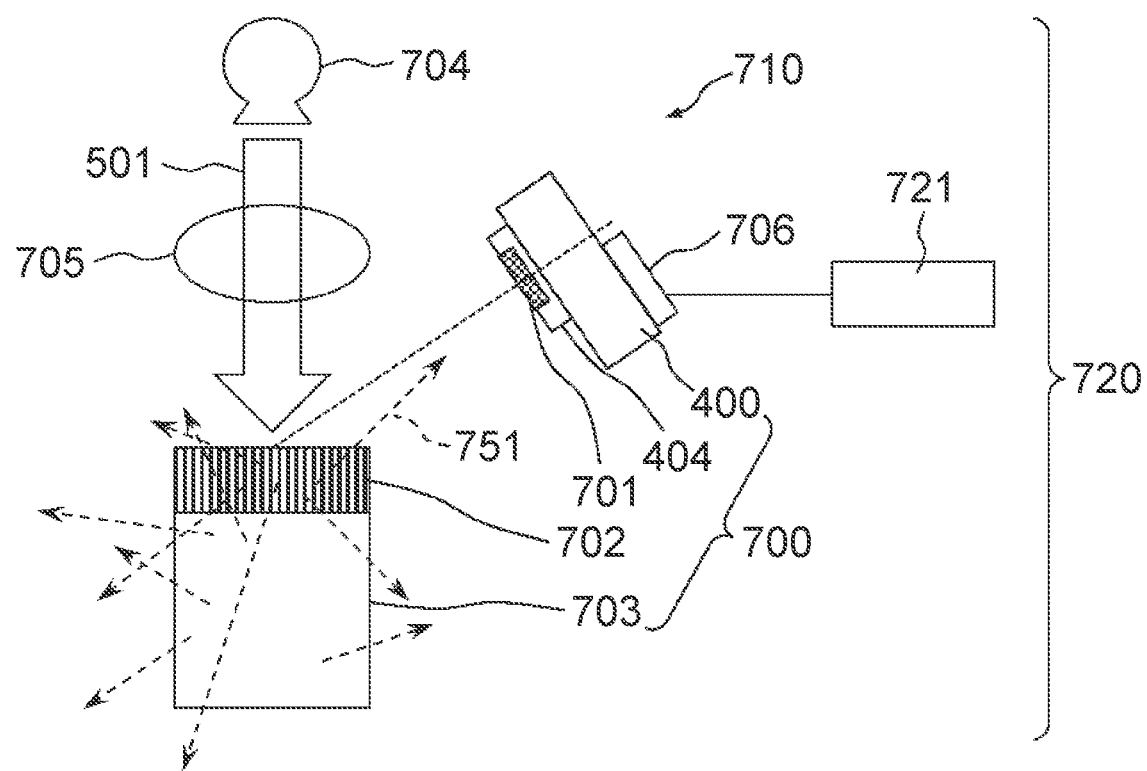
FIG. 10 is a view showing an example of the arrangement of a radiation detector using the circuit board, a radiation detection apparatus, and an inspection apparatus according to the embodiment.

In the arrangement shown in FIG. 10, the radiation 501 emitted from the radiation source 704 to the scintillator 702 of the radiation detector 700 via the object 705 is configured not to directly enter the circuit board 400 on which the semiconductor package 404 is mounted. More specifically, the light generated by the scintillator 702 due to the incidence of the radiation 501 is acquired by the light-receiving element 701 arranged at a position away from the optical axis of the radiation 501. This can suppress damage, by the radiation 501, to the integrated circuit 414 mounted on the semiconductor package 404.

However, the radiation 501 entering the scintillator 702 of the radiation detector 700 via the object 705 may be scattered in the scintillator 702 or a base 703 that supports the scintillator 702, thereby generating a scattered ray 751. Furthermore, the scattered ray 751 may enter the circuit board 400. However, even if the scattered ray 751 enters the circuit board 400, the circuit board 400 has a structure in which the wiring layer 402 where no conductor 412 is arranged in the region overlapping the integrated circuit 414 included in the semiconductor package 404 is arranged, as described above. This suppresses further backscattering of the scattered ray 751 in the circuit board 400, thereby making it possible to suppress damage to the integrated circuit 414 mounted on the semiconductor package 404.

Furthermore, an inspection apparatus 720 may be formed by combining, with the radiation detection apparatus 710, a determiner 721 that determines the quality of the object 705 using radiation image data generated by the radiation detection apparatus 710 including the circuit board 400 according to this embodiment. The inspection apparatus 720 may be an inspection apparatus that inspects the object 705 moving between the radiation source 704 and the radiation detector 700 using, for example, a sensor chip (line sensor) including the linear scintillator 702 and the linear light-receiving element 701.

Another embodiment using the linear scintillator 104 and the linear sensor element 102 (line sensor) will be described next. For radiation inspection of an inspection target, a radiation detector including a scintillator for converting radiation into light and a line sensor for detecting the light is used. To inspect a larger inspection target, the radiation detector is configured to detect radiation entering a line (called a scan line) longer than the inspection target at once. Since, however, the long line sensor is expensive, there is known a method of using a plurality of inexpensive line sensors in combination. For example, PTL 2 discloses the use of a plurality of line sensors in each of which phosphors for converting X-rays into light are stacked. According to PTL 2, to prevent a dead zone from being generated between the line sensors, the line sensors are arranged to partially overlap each other in the incident direction of the X-rays.

Since the line sensors are provided to partially overlap each other in the incident direction of the X-rays in the radiation detector described in PTL 2, the distance from the inspection target to the phosphor is different for each line sensor. In general, radiation from a radiation source is not completely parallel, the radiation detector described in PTL 2 has a problem that the magnification of an image of the inspection target is different for each line sensor.

Figure 11A:
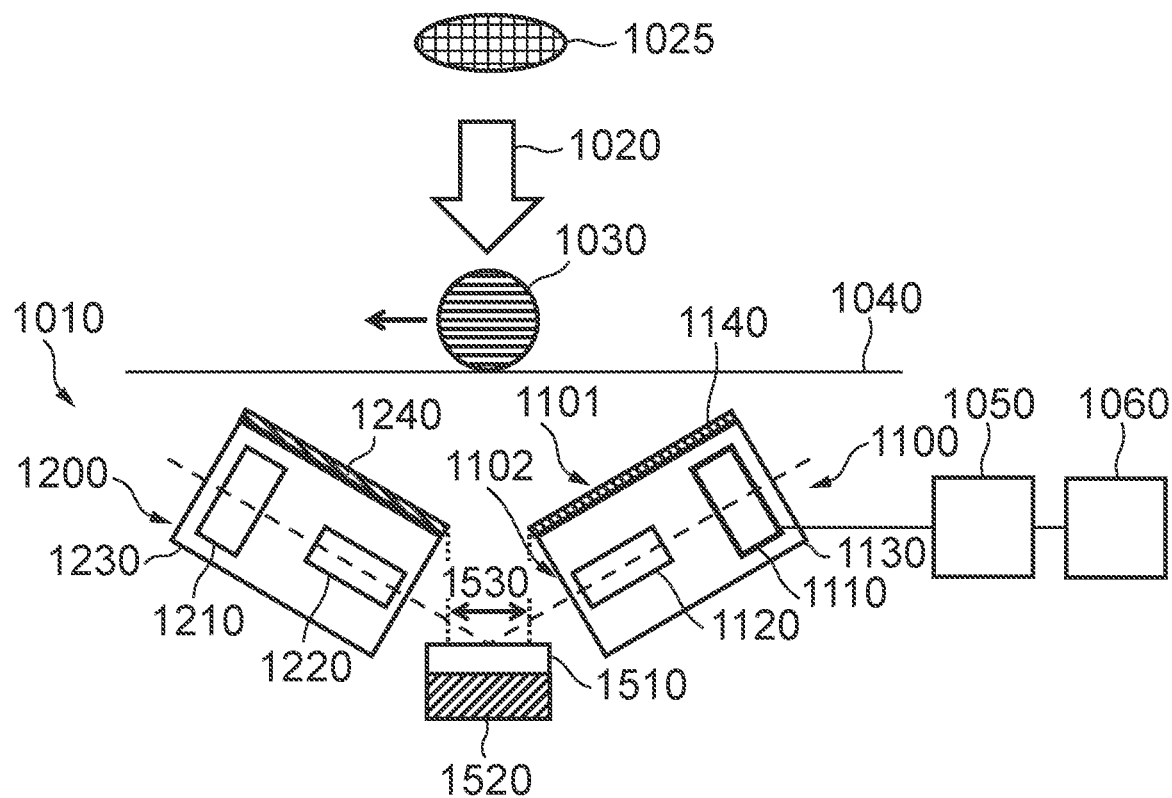
FIG. 11A is a schematic view of a radiation detector according to the embodiment.

A radiation detector according to an embodiment of the present invention includes a scintillator, a first line sensor, and a second line sensor. A radiation detector 1010 (electromagnetic wave detector) according to the embodiment of the present invention will be described below with reference to FIGS. 11A and 12A. The radiation detector 1010 has a long structure extending in the longitudinal direction, and can detect radiation entering a scan line extending in the longitudinal direction at once. The radiation detector 1010 can detect, for example, radiation 1020 such as X-rays having passed through an object 1030 as a measurement target on a measurement surface 1040. FIG. 11A is a sectional view of the radiation detector 1010 in a section perpendicular to the longitudinal direction.

A scintillator 1510 extends along the first axis, and can convert the incident radiation 1020 into light. The first axis is an axis parallel to the longitudinal direction of the radiation detector 1010, and thus the scintillator 1510 has a structure extending in the longitudinal direction. All or part of the scintillator 1510 serves as a scan line extending in the longitudinal direction to detect incident radiation on this portion. For example, the scintillator 1510 can generate light of a wavelength of 350 nm to 800 nm with a luminance corresponding to the dose of the incident radiation. The scintillator 1510 may have a continuous integrated structure so as to obtain a continuous image by light generated on the scintillator 1510.

As shown in FIG. 11A, the scintillator 1510 may be provided on a base material 1520. In one embodiment, the scintillator 1510 is sintered on the base material 1520. The scintillator 1510 may have isotropic light emission characteristics like a phosphor made of GOS ($Gd_2O_2S$). In this case, as shown in FIG. 11A, the scintillator 1510 can be provided on the surface of the base material 1520 on the side of line sensors 1100 and 1200. The scintillator 1510 can be provided on the surface of the base material 1520 on the incident side of the radiation 1020. With this arrangement, the line sensors 1100 and 1200 can detect the light generated upon the incidence of the radiation 1020 on the surface of the scintillator 1510, thereby improving detection efficiency.

The line sensor 1100 as the first line sensor has a structure extending along the second axis parallel to the first axis. The second axis is an axis parallel to the longitudinal direction of the radiation detector 1010, and thus the line sensor 1200 also has a structure extending in the longitudinal direction. On the other hand, the length of the line sensor 1100 in the longitudinal direction may be shorter than the scintillator 1510, and may be, for example, a half or less.

Figure 12A:
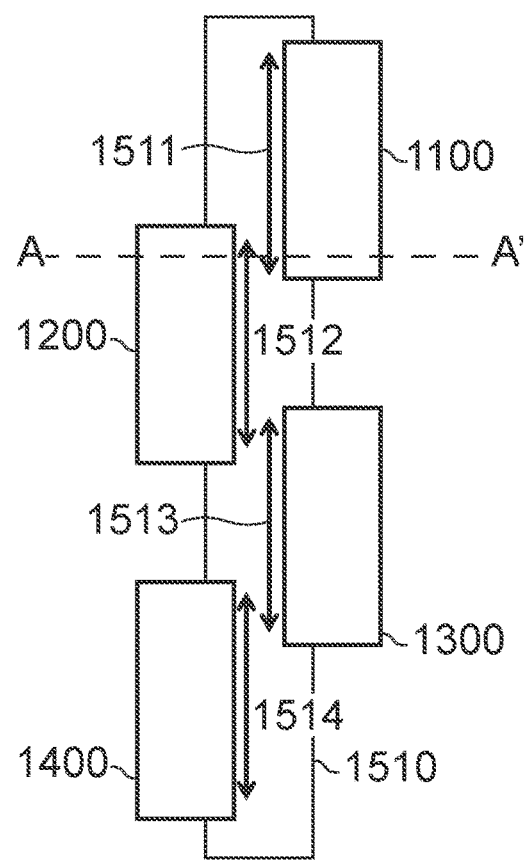
FIG. 12A is a schematic view of the radiation detector according to the embodiment.

The positional relationship between the line sensor 1100 and the scintillator 1510 will be described with reference to FIG. 12A. FIG. 12A shows the arrangement of the line sensor 1100 and the scintillator 1510 when viewed from the incident direction of the radiation 1020. FIG. 11A corresponds to a sectional view at a position of A-A' in FIG. 12A. The line sensor 1100 can detect light from a first region 1511 of the scintillator 1510. In this example, the line sensor 1100 can detect light from the first region 1511 extending in the longitudinal direction at once but need not have a detection surface for detecting light in each end portion of the line sensor 1100 in the longitudinal direction. Therefore, the length of the first region 1511 may be shorter than that of the line sensor 1100.

The line sensor 1100 may include a sensor element 1110 and a lens portion 1120. The sensor element 1110 converts the light generated by the scintillator 1510 into an electrical signal. The sensor element 1110 can include, for example, a photoelectric conversion element and a switch element formed on a semiconductor substrate made of silicon or the like. The sensor element 1110 may also have a structure extending in the longitudinal direction along the second axis, and can detect light from the first region 1511 of the scintillator 1510 at once.

The lens portion 1120 is located between the scintillator 1510 and the sensor element 1110, and forms an image of the light generated by the scintillator 1510 on the sensor element 1110. The lens portion 1120 may be, for example, a rod lens array. Each rod lens included in the rod lens array extends in the direction from the scintillator 1510 to the sensor element 1110. Furthermore, the plurality of rod lenses are arrayed in the longitudinal direction of the sensor element 1110. The lens portion 1120 having this arrangement can form an image of the light from the first region 1511 extending in the longitudinal direction on the sensor element 1110 extending in the longitudinal direction. Each rod lens may be, for example, a SELFOC® lens.

The line sensor 1100 may further include a frame 1130. In this case, the sensor element 1110 and the lens portion 1120 may be fixed to the frame 1130. (The frame 1130 can be the above-described housing 107). The structure of the frame 1130 is not particularly limited, and the frame 1130 may be made of, for example, a metal, a resin, or the like. The frame 1130 may contain, for example, a metal such as lead to protect the sensor element 1110 and the like from radiation.

The line sensor 1200 as the second line sensor has a structure extending along the third axis parallel to the first axis. The third axis is an axis parallel to the longitudinal direction of the radiation detector 1010, and thus the line sensor 1200 also has a structure extending in the longitudinal direction. On the other hand, the third axis is different from the second axis. That is, the line sensors 1100 and 1200 are arranged at different positions in a section perpendicular to the longitudinal direction. In one embodiment, the direction from the first axis to the second axis is different from the direction from the first axis to the third axis. Therefore, line sensors 1100 and 1200 can detect, from different directions, the light generated by the scintillator 1510. This means that the line sensors 1100 and 1200 can simultaneously detect the light from the same position on the scintillator 1510.

On the other hand, the line sensor 1200 may have the same arrangement as that of the line sensor 1100 except for the location. That is, the line sensor 1200 may include a sensor element 1210, a lens portion 1220, and a frame 1230, similar to the line sensor 1100.

Referring to FIG. 12A, the line sensor 1200 can detect light from a second region 1512 of the scintillator 1510. That is, the line sensor 1200 can detect light from the second region 1512 extending in the longitudinal direction at once. Similar to the line sensor 1100, the line sensor 1200 need not have a detection surface for detecting light in each end portion of the line sensor 1200 in the longitudinal direction. Therefore, the length of the second region 1512 may be shorter than that of the line sensor 1200.

The first region 1511 and the second region 1512 are different regions but are arranged along the first axis and partially overlap each other. In other words, light from the overlapping region of the first region 1511 and the second region 1512 can be detected by both the line sensors 1100 and 1200. Therefore, with this arrangement, it is possible to detect, by a combination of the short line sensors 1100 and 1200, light from the entire range of the long region across the first region 1511 and the second region 1512 on the scintillator 1510. Therefore, it is easy to decrease the region on the scan line, where the generated light is not detected. On the other hand, with this arrangement, the first region 1511 and the second region 1512 where light is generated are continuous, and it is thus easy to equalize the distances from the measurement surface 1040 to the first region 1511 and the second region 1512. Therefore, the magnification of the image of the object 1030 by the light generated on the scintillator 1510 can be made constant between the first region 1511 and the second region 1512. To implement this arrangement, in one embodiment, the projection of the line sensor 1100 on the first axis overlaps the projection of the line sensor 1200 on the first axis.

The radiation detector 1010 may include two or more line sensors extending along the second axis. In the example shown in FIG. 12A, in addition to the line sensor 1100, the radiation detector 1010 includes a line sensor 1300 as the third line sensor extending along the second axis. The line sensor 1300 can have the same arrangement as that of the line sensor 1100. The line sensor 1300 can detect light from a third region 1513 of the scintillator 1510. As shown in FIG. 12A, the second region 1512 and the third region 1513 may partially overlap each other. With this arrangement, it is possible to simultaneously detect light from a longer range across the first region 1511 to the third region 1513. That is, it is possible to make the scan line longer. As shown in FIG. 12A, since the line sensor 1200 can detect light from the second region 1512, there may be provided a gap between the first region 1511 and the third region 1513. That is, the line sensors 1100 and 1300 may be spaced apart from each other.

Figure 12B:
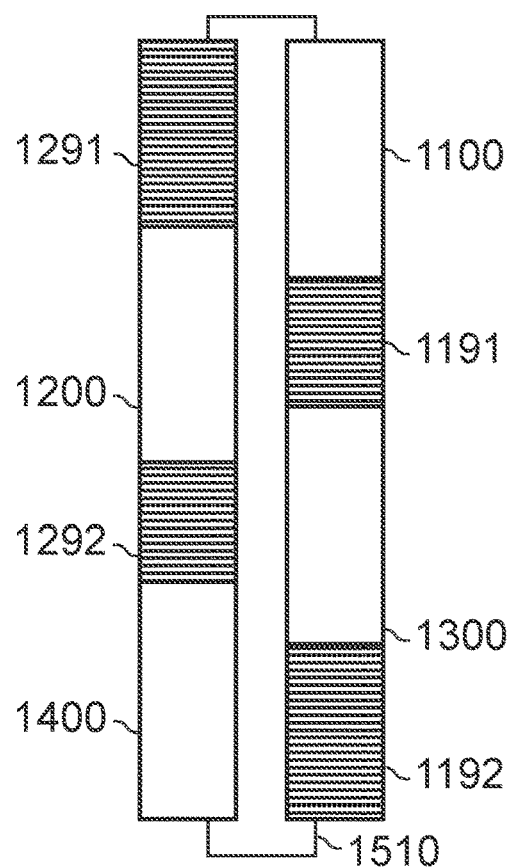
FIG. 12B is a schematic view of the radiation detector according to the embodiment.

Furthermore, as shown in FIG. 12B, the line sensors 1100 and 1300 may be connected via a connecting portion 1191 that does not detect light from the scintillator 1510 and extends along the second axis. The connecting portion 1191 may be a frame (dummy frame) having the same rigidity as that of the line sensor 1100. With this arrangement, since the rigidity along the second axis becomes almost uniform, deformation caused by a temperature change or the like is readily prevented. As shown in FIG. 12B, another connecting portion 1192 extending along the second axis may be provided.

Similarly, the radiation detector 1010 may have two or more line sensors extending along the third axis. In the example shown in FIG. 12A, in addition to the line sensor 1200, the radiation detector 1010 includes a line sensor 1400 as the fourth line sensor extending along the third axis. The line sensor 1400 can detect light from a fourth region 1514 of the scintillator 1510, and can have the same arrangement as that of the line sensor 1200. Furthermore, as shown in FIG. 12B, the radiation detector 1010 may include a connecting portion 1291 and a connecting portion 1292 that extends along the third axis, connects the line sensors 1200 and 1400, and does not detect light from the scintillator 1510.

The first angle formed by the surface of the scintillator 1510 and the optical axis of an optical element for collecting light detected by the line sensor 1100 may match the second angle formed by the surface of the scintillator 1510 and the optical axis of an optical element for collecting light detected by the line sensor 1200. In this embodiment, the optical element for collecting light detected by the line sensor 1100 is the lens portion 1120, and the optical element for collecting light detected by the line sensor 1200 is the lens portion 1220. That is, the optical axis of the lens portion 1120 and that of the lens portion 1220 may have the same tilt with respect to the surface of the scintillator 1510. Furthermore, the line sensors 1100 and 1200 may detect light beams emitted in directions having equal angles with respect to the incident direction of the radiation. For example, on a surface perpendicular to the first axis, an angle formed by the incident direction of the radiation and the traveling direction of light traveling from the first axis to the first line sensor may match an angle formed by the incident direction of the radiation and the traveling direction of light traveling from the first axis to the second line sensor. With this arrangement, images detected by the line sensors 1100 and 1200 have a smaller difference.

The above-described first and second angles may be 45° or less, or 30° or less. For example, on the surface perpendicular to the first axis, the angle formed by the incident direction of the radiation and the traveling direction of light traveling from the first axis to the first line sensor and the second angle formed by the incident direction of the radiation and the traveling direction of light traveling from the first axis to the second line sensor may respectively be 45° or more, or 60° or more. With this arrangement, as shown in FIG. 11A, the sensor elements 1110 and 1210 are arranged away from a space around the scintillator 1510 through which more radiation 1020 passes. This can suppress degradation of the sensor element 1110 or 1210 caused by radiation.

In the example shown in FIGS. 11A and 12A, the radiation 1020 that has been emitted from a radiation source 1025 and passed through the object 1030 passes through a portion between the line sensors 1100 and 1200. In this arrangement, to prevent degradation of the line sensor 1100 caused by radiation, the radiation detector 1010 may further include a radiation shielding material provided between the radiation source 1025 and the line sensor 1100. This radiation shielding material may be provided at a position closer to the radiation source 1025 than the object 1030, or may be provided adjacent to the object 1030. On the other hand, in the example shown in FIG. 11A, a radiation shielding material 1140 is provided in the line sensor 1100. For example, the line sensor 1100 may have a surface 1101 facing the incident radiation or facing in the direction of the radiation source, and the radiation shielding material 1140 may be provided on the surface 1101. In the example shown in FIG. 11A, the radiation shielding material 1140 is provided on the surface of the frame 1130 facing the incident radiation. On the other hand, another surface of the line sensor 1100 is made to face the scintillator 1510 to receive light from the scintillator 1510. Note that a collimator (not shown) or the like may prevent the radiation 1020 from directly entering the line sensor 1100. In this case as well, the radiation shielding material 1140 can prevent scattered radiation or the like from entering the line sensor 1100.

Furthermore, the radiation shielding material 1140 may limit a radiation incident range on the scintillator 1510. In this arrangement, the radiation shielding material 1140 functions as a collimator that limits the radiation incident range on the scintillator 1510. Since the radiation shielding material 1140 is close to the scintillator 1510, it can limit the radiation incident range on the scintillator 1510 more accurately, as compared with, for example, the collimator arranged adjacent to the measurement surface 1040.

Note that it is possible to obtain such effect even when the line sensors 1100 and 1200 are not used concurrently. That is, in another embodiment, a radiation detector includes the scintillator 1510 extending along the first axis and the line sensor 1100 that detects light from the scintillator 1510. In this case, the line sensor 1100 includes the radiation shielding material 1140 facing incident radiation. This radiation shielding material 1140 may limit the radiation incident range on the scintillator 1510.

The radiation detector 1010 may include a radiation shielding material provided between the radiation source 1025 and the line sensor 1200. Similar to the line sensor 1100, a radiation shielding material 1240 may be provided in the line sensor 1200, and may limit the radiation incident range on the scintillator 1510.

Figure 11B:
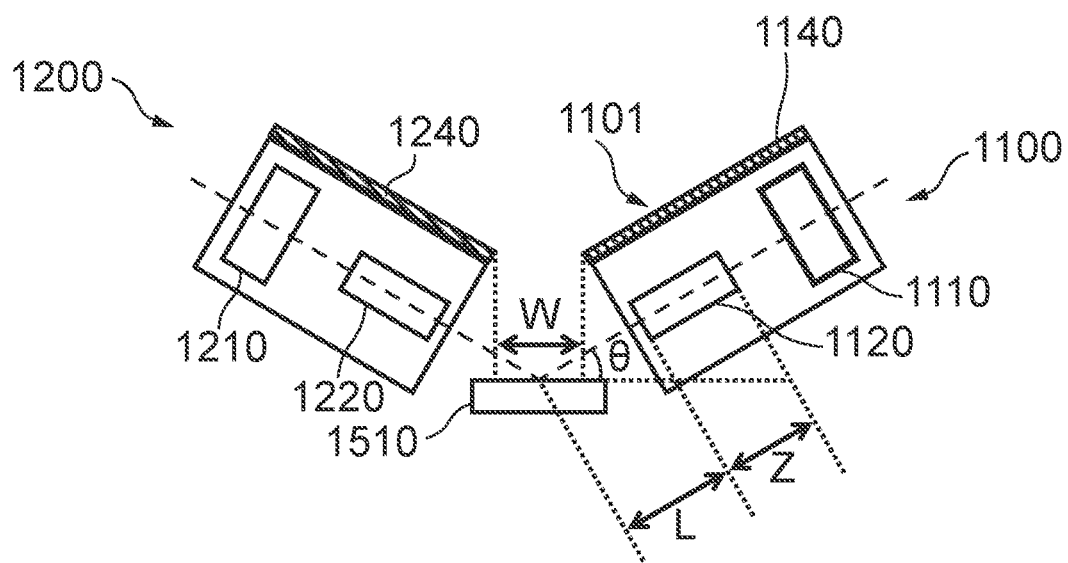
FIG. 11B is a schematic view of the radiation detector according to the embodiment.

In one embodiment, an interval W between the radiation shielding materials 1140 and 1240, that is, a beam width in a direction perpendicular to the longitudinal direction of radiation entering the scintillator 1510 can be decided, as follows. This arrangement can further suppress degradation of the sensor element 1110 or 1210 caused by radiation.

$$A/2 < W/2 < (L+Z)\cos\theta \quad (12)$$

where Z represents the length of the lens portion 1120 or 1220, and L represents the distance (the distance along the optical axis or optical axis center of the lens portion 1120) from the lens portion 1120 or 1220 to the scintillator 1510, as shown in FIG. 11B that shows part of FIG. 11A. Furthermore, A represents the pixel size (pixel pitch) of the sensor element 1110 or 1210 in the sub-scanning direction (the direction perpendicular to the longitudinal direction), and $\theta$ represents the tilt of the optical axis of the lens portion 1120 or 1220 with respect to the surface of the scintillator 1510. In this example, if the surface of the scintillator is not flat, $\theta$ may represent an angle formed by the surface and the optical axis of the lens portion in a portion where the optical axis (an extension thereof) and the scintillator surface intersect each other. Alternatively, $\theta$ may represent an angle formed by the optical axis of the lens portion and a plane perpendicular to the direction in which radiation (X-rays) enters the scintillator.

The interval W can be decided to satisfy $$A/2 < W/2 < (L+Z/2)\cos\theta \quad (13)$$

Furthermore, the interval W can be decided to satisfy $$A/2 < W/2 < L\cos\theta \quad (14)$$

With these arrangements, it is possible to further suppress degradation of the lens portion 1120 or 1220 caused by radiation.

Figure 13:
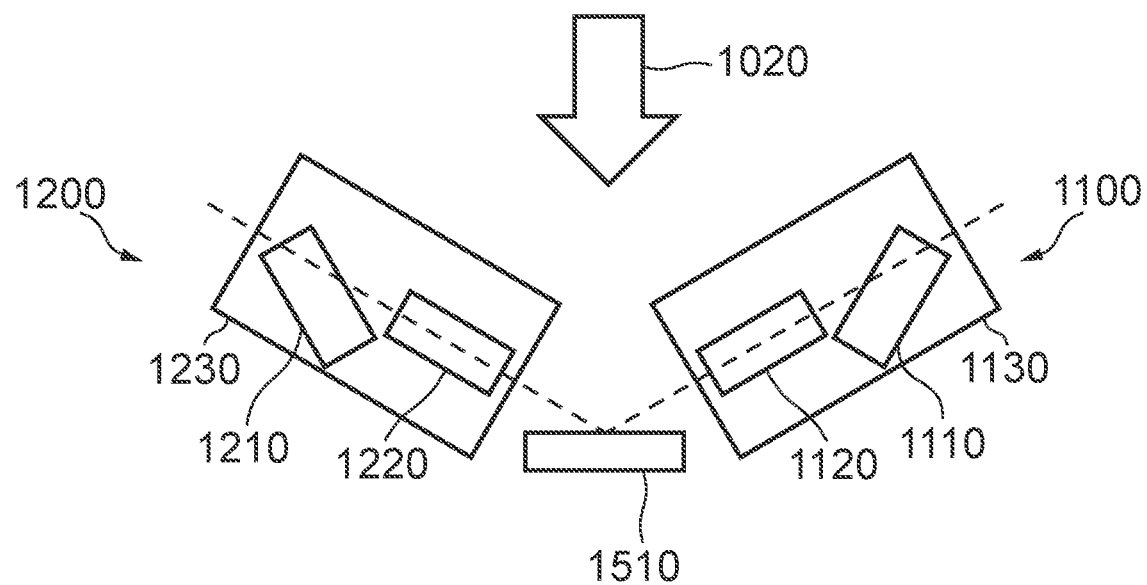
FIG. 13 is a schematic view of the radiation detector according to the embodiment.

In one embodiment, the sensor element 1110 of the line sensor 1100 includes a detection surface for detecting light from the first region 1511, and the normal direction of the detection surface tilts with respect to the direction from the line sensor 1100 to the first axis. FIG. 13 shows this embodiment. As shown in FIG. 13, when light from the scintillator 1510 is measured from a direction tilting with respect to the surface of the scintillator 1510, it is possible to obtain a more satisfactory image by tilting the detection surface of the sensor element 1110 in accordance with that tilt. At this time, the tilt direction of the detection surface with respect to the direction from the line sensor 1100 to the first axis may be opposite to the tilt direction of the surface of the scintillator 1510 with respect to the direction from the line sensor 1100 to the first axis. The tilt amount (angle) of the detection surface and the tilt amount (angle) of the surface of the scintillator 1510 are less than 90°. If the lens portion 1120 is a lens that gives an erect image, the tilt amount of the detection surface with respect to the direction from the line sensor 1100 to the first axis can be made equal to the tilt amount of the surface of the scintillator 1510 with respect to the direction from the line sensor 1100 to the first axis. Similarly, the sensor element 1210 of the line sensor 1200 may include a detection surface for detecting light from the second region 1512. The normal direction of the detection surface may tilt with respect to the direction from the line sensor 1200 to the first axis. The tilt direction of the detection surface with respect to the direction from the line sensor 1200 to the first axis may be opposite to the tilt direction of the surface of the scintillator 1510 with respect to the direction from the line sensor 1200 to the first axis. If the lens portion 1220 is a lens that gives an erect image, the tilt amount of the detection surface with respect to the direction from the line sensor 1200 to the first axis can be made equal to the tilt amount of the surface of the scintillator 1510 with respect to the direction from the line sensor 1200 to the first axis.

Figure 14A:
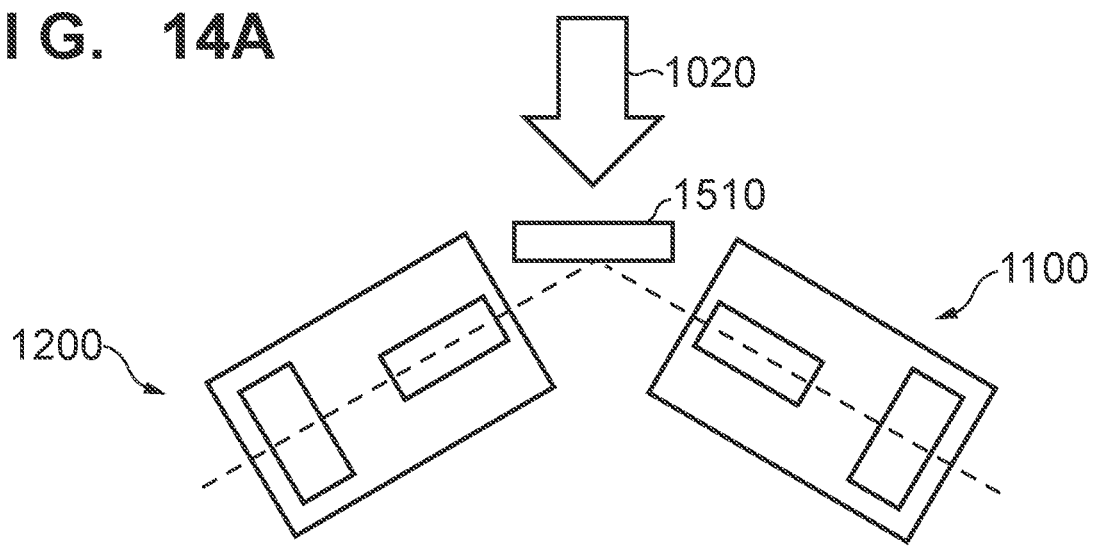
FIG. 14A is a schematic view of the radiation detector according to the embodiment.
Figure 14B:
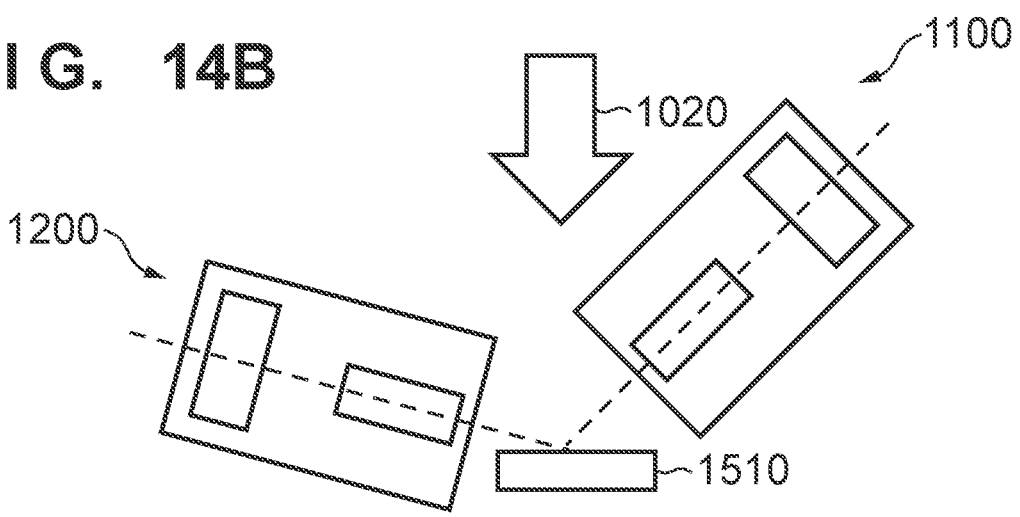
FIG. 14B is a schematic view of the radiation detector according to the embodiment.
Figure 14C:
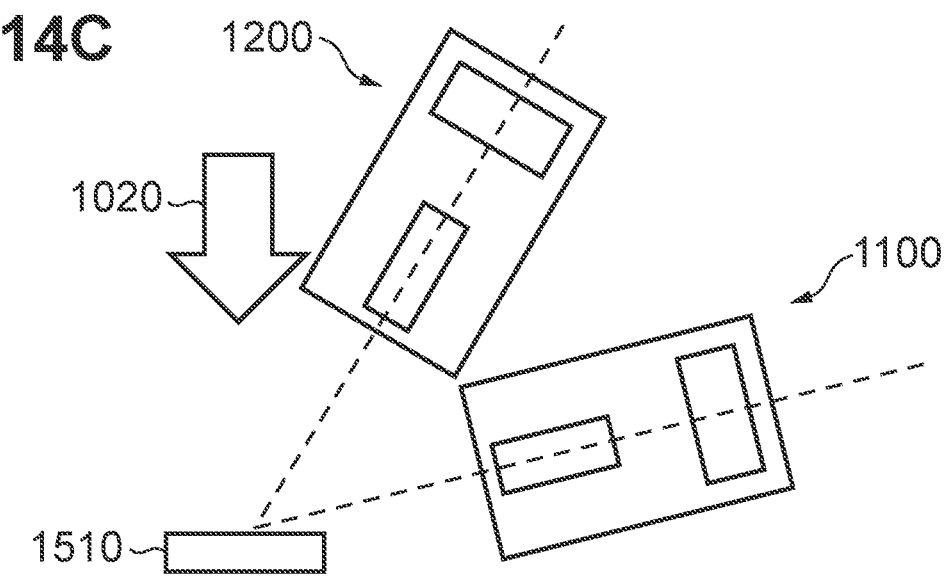
FIG. 14C is a schematic view of the radiation detector according to the embodiment.

The arrangement of the line sensors 1100 and 1200 or the arrangement of the second and third axes is not limited to the example shown in FIGS. 11A and 12A. FIGS. 14A to 14C show other examples of the arrangement of the line sensors 1100 and 1200. As shown in FIG. 14A, the line sensors 1100 and 1200 may be arranged to face a surface of the scintillator 1510 on the opposite side of a surface which receives the radiation 1020. As shown in FIG. 14B, the line sensors 1100 and 1200 may be arranged so that the optical axes of the line sensors 1100 and 1200 have different tilts with respect to the surface of the scintillator 1510 or the incident direction of the radiation 1020. As shown in FIG. 14C, the line sensors 1100 and 1200 may be arranged, in a plane perpendicular to the first axis, in the same region out of two regions divided by a region through which the radiation 1020 passes. In the case shown in FIG. 14C, it is possible to prevent the radiation 1020 from passing through a portion between the line sensors 1100 and 1200.

Figure 15A:
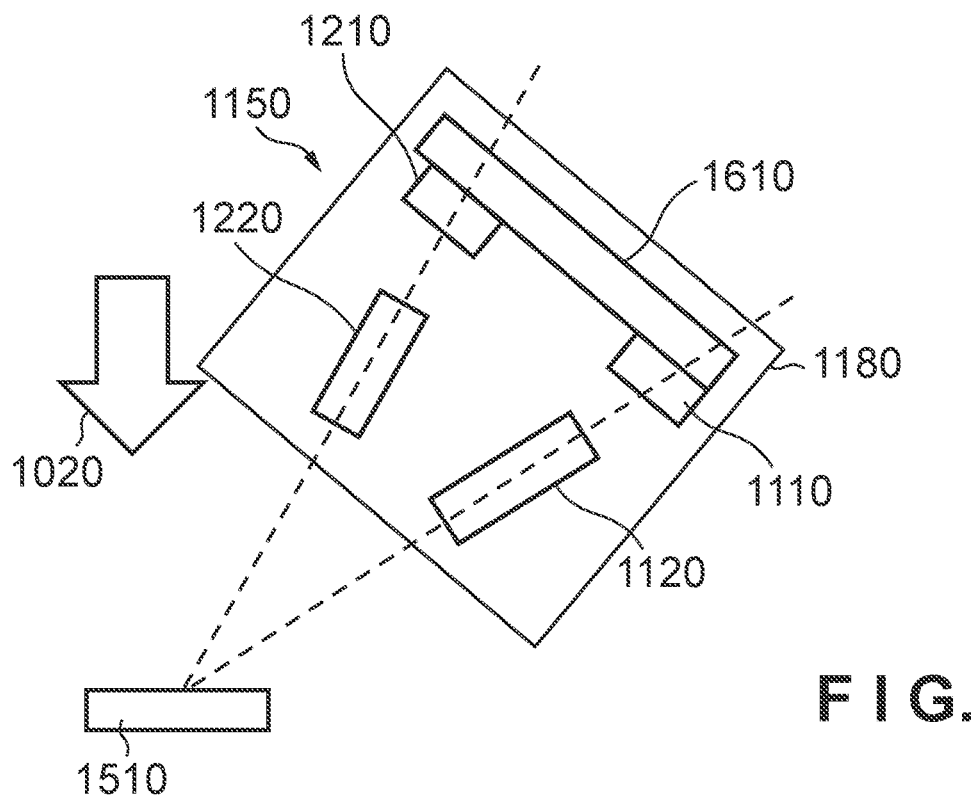
FIG. 15A is a schematic view of the radiation detector according to the embodiment.

FIG. 15A is a view of a line sensor 1150 showing a modification of FIG. 14C. The radiation detector 1010 is not limited to the arrangement that requires the two separate line sensors 1100 and 1200, as in each of the above-described embodiments. As shown in FIG. 15A, in the radiation detector 1010, the two sensor elements 1110 and 1210 arranged on one substrate 1610 (which can be the above-described base 101 or circuit board 400) and the lens portions 1120 and 1220 corresponding to the two sensor elements 1110 and 1210, respectively, may be arranged in one frame 1180. The sensor elements 1110 and 1210 may be implemented on different substrates arranged in the frame 1180.

Figure 15B:
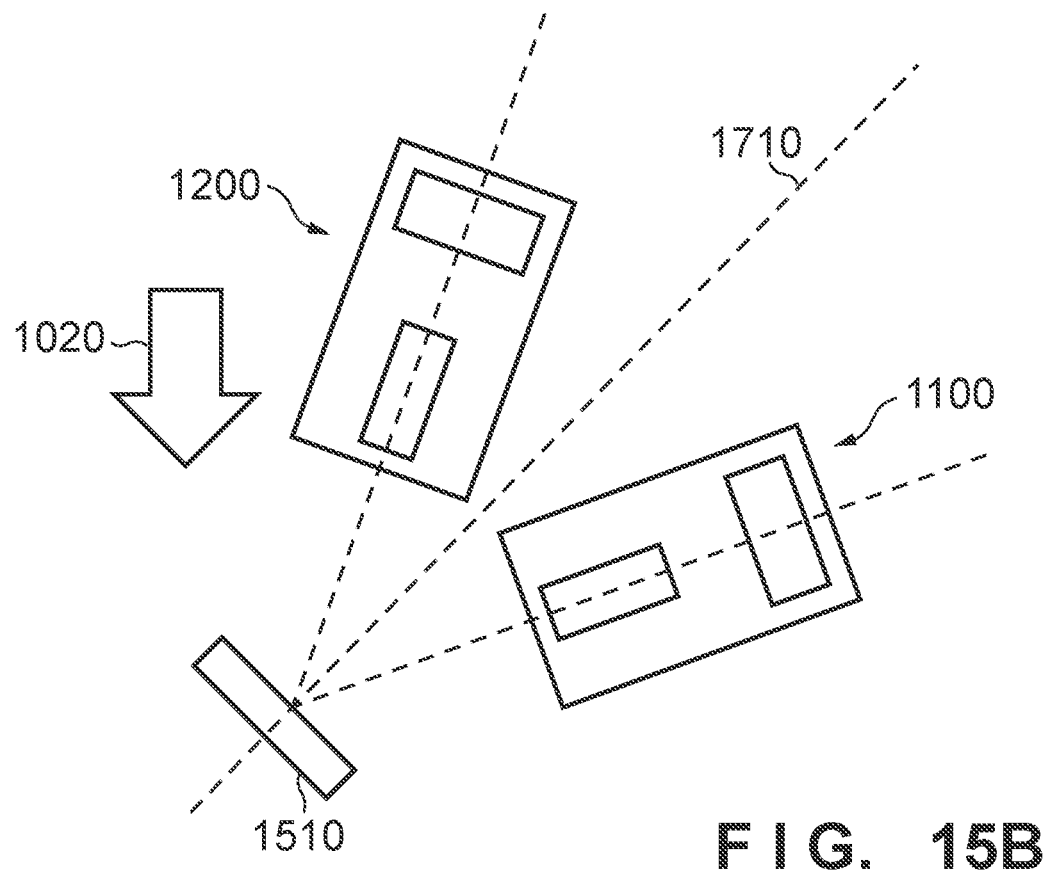
FIG. 15B is a schematic view of the radiation detector according to the embodiment.

FIG. 15B is a view showing a modification of FIG. 14C. A normal 1710 of a surface of the scintillator 1510 which receives radiation may tilt with respect to the incident direction of the radiation 1020. At this time, the difference between the angle formed by the normal 1710 and the optical axis of the lens portion 1120 and the angle formed by the normal 1710 and the optical axis of the lens portion 1220 may be 3° or less, or 1° or less. Furthermore, the angle formed by the normal 1710 and the optical axis of the lens portion 1120 may be equal to the angle formed by the normal 1710 and the optical axis of the lens portion 1220. By equalizing the angles formed by the normal 1710 and the optical axes of the lens portions 1120 and 1220, respectively, it is possible to suppress not only a difference in size between images of the inspection target obtained by the two sensor elements 11120 and 1210 but also a difference in resolution (MTF), as compared with the arrangement shown in FIG. 14C.

The radiation detector 1010 can be used as a constituent element of a radiation inspection apparatus. FIG. 11A also shows such radiation inspection apparatus. The radiation inspection apparatus shown in FIG. 11A includes the radiation detector 1010 and the radiation source 1025. Radiation emitted from the radiation source 1025 passes through the object 1030 between the radiation source 1025 and the radiation detector 1010 to enter the scintillator 1510. By placing the object 1030 on the measurement surface 1040 and moving the object 1030 on the measurement surface 1040, the overall object 1030 can be irradiated with the radiation, thereby performing inspection.

The line sensors 1100 and 1200 are connected to an image generation processor 1050 that generates a radiation image based on electrical signals generated when the sensor elements 1110 and 1210 receive light from the scintillator 1510. Note that the image generation processor 1050 may be included in the radiation detector 1010 or an external information processing apparatus. In this way, the radiation inspection apparatus can obtain a radiation image of the object. The radiation inspection apparatus may further include a determiner 1060 that determines the quality of the object 1030 using the radiation image data. Note that FIG. 11A does not illustrate connection between the sensor element 1210 and the image generation processor 1050 and determiner 1060.

The present invention is not limited to the above-described embodiments. The above-described embodiments can appropriately be combined and used, as a matter of course, and various modifications and changes can be made to each of the above-described embodiments within the spirit and scope of the present invention. For example, the detection target by the detector of each of the above-described embodiments is radiation. The present invention, however, is not limited to this, and the detection target may be an electromagnetic wave or ultraviolet rays (electromagnetic wave) of a wavelength of 10 nm (inclusive) to 400 nm (inclusive). That is, the detection target may be any electromagnetic wave. However, the present invention effectively functions for an electromagnetic wave of a wavelength shorter than that in a visible light region (400 to 700 nm), and an electromagnetic wave of a wavelength of 150 nm or less may be possible. More specifically, a large effect is obtained when detecting the radiation described in the embodiments, more particularly, X-rays. Note that radiation is a collective term for particle radiation such as α-rays, β-rays, a neutron beam, a proton beam, a heavy ion beam, and a meson beam and electromagnetic waves (electromagnetic radiation) such as γ-rays and X-rays.

According to the above-described means, a technique advantageous in suppressing damage to a sensor element caused by an electromagnetic wave in an electromagnetic wave detector is provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An electromagnetic wave detector comprising:
   a base;
   a sensor element arranged on a principal surface of the base and configured to convert, into an electrical signal, light emitted from a scintillator which receives an electromagnetic wave;
   a lens portion arranged between the scintillator and the sensor element and configured to collect the light generated by the scintillator to the sensor element;
   a light transmissive portion arranged between the lens portion and the sensor element and configured to transmit the light generated by the scintillator; and
   a shielding portion including an inner wall located on a periphery of the sensor element and configured to shield the electromagnetic wave,
   wherein the inner wall is arranged between the light transmissive portion and the principal surface.

2. The electromagnetic wave detector according to claim 1, wherein the sensor element is sealed by the principal surface, the light transmissive portion, and the shielding portion.

3. The electromagnetic wave detector according to claim 1, wherein
   an upper surface of the shielding portion on an opposite side of a surface contacting the principal surface and an opposite surface of the light transmissive portion facing the principal surface are in contact with each other, and
   in an orthogonal projection with respect to the principal surface, a contact portion between the upper surface and the opposite surface surrounds the sensor element.

4. The electromagnetic wave detector according to claim 3, wherein
   if μg represents a mass absorption coefficient of the light transmissive portion, μs represents a mass absorption coefficient of the shielding portion, and in a section passing through the sensor element and perpendicular to the principal surface of the base, X represents a shortest length of the portion where the shielding portion and the light transmissive portion are in contact with each other and Tg represents a thickness of the light transmissive portion, $$0.01 \le e^{-\mu_s X}/e^{-\mu_g T_g} \le 10$$

is satisfied.

5. The electromagnetic wave detector according to claim 3, wherein
   if μg represents a mass absorption coefficient of the light transmissive portion, and in a section passing through the sensor element and perpendicular to the principal surface of the base, X represents a shortest length of the portion where the shielding portion and the light transmissive portion are in contact with each other and Tg represents a thickness of the light transmissive portion, $$0.01 \le e^{-\mu_g X}/e^{-\mu_g T_g} \le 10$$

is satisfied.

6. The electromagnetic wave detector according to claim 1, wherein
the inner wall of the shielding portion and a side wall of the light transmissive portion are in contact with each other, and
in an orthogonal projection with respect to the principal surface, contact portions between the inner wall and the side wall surround the sensor element.

7. The electromagnetic wave detector according to claim 6, wherein
if µg represents a mass absorption coefficient of the light transmissive portion, µs represents a mass absorption coefficient of the shielding portion, Ws represents a shortest length between an outer wall and the inner wall of the shielding portion in a section passing through the sensor element and perpendicular to the principal surface of the base, and Tg represents a thickness of the light transmissive portion, $$0.01 \le e^{-\mu_s W_s}/e^{-\mu_g T_g} \le 10$$

is satisfied.

8. The electromagnetic wave detector according to claim 1, wherein
if L represents a distance between the principal surface and a surface of the lens portion facing the principal surface, θ represents an aperture angle of the lens portion, and W represents a shortest distance between an optical axis of the lens portion and the inner wall of the shielding portion in a section passing through the sensor element and perpendicular to the principal surface of the base, $$0.6 \le W/(L \times \tan\theta) \le 5$$

is satisfied.

9. The electromagnetic wave detector according to claim 8, wherein
the sensor element is a linear sensor element including a longitudinal direction and a widthwise direction orthogonal to the longitudinal direction, and
the shortest distance W between the optical axis of the lens portion and the inner wall of the shielding portion is a distance in the widthwise direction.

10. The electromagnetic wave detector according to claim 1, wherein a reflectance of the inner wall of the shielding portion with respect to the light generated by the scintillator is not higher than 10%.

11. The electromagnetic wave detector according to claim 1, wherein the light transmissive portion contains glass added with at least one of lead and bismuth.

12. The electromagnetic wave detector according to claim 1, wherein the shielding portion contains a resin containing a metal.

13. The electromagnetic wave detector according to claim 12, wherein the metal includes tungsten.

14. The electromagnetic wave detector according to claim 1, wherein the shielding portion is an elastic body.

15. The electromagnetic wave detector according to claim 1, wherein the light transmissive portion and the shielding portion are integrally made of the same material.

16. The electromagnetic wave detector according to claim 1, wherein the shielding portion and the base are integrally made of the same material.

17. The electromagnetic wave detector according to claim 1, wherein
the sensor element is arranged at a position not overlapping an optical axis of the lens portion, and
the light transmissive portion has an effect of refracting a light beam, that has been generated by the scintillator and passed through the optical axis of the lens portion, to enter the sensor element.

18. The electromagnetic wave detector according to claim 1, further including a lens fixing portion arranged to contact a side surface of the lens portion and cover the light transmissive portion, wherein
an electromagnetic wave absorptance of the lens fixing portion is higher than an electromagnetic wave absorptance of the lens portion.

19. The electromagnetic wave detector according to claim 1, wherein
the base includes at least one wiring layer, and
in an orthogonal projection with respect to the principal surface, one of the at least one wiring layer is a wiring layer in which a ratio of an area of a portion, where a conductor forming a wiring pattern is arranged, with respect to a region overlapping the sensor element is not higher than 20%.

20. The electromagnetic wave detector according to claim 1, wherein
the sensor element is arranged at a position not overlapping an optical axis of the lens portion, and
the light transmissive portion has an effect of refracting a light beam, that has been generated by the scintillator and passed through the optical axis of the lens portion, to enter the sensor element.

21. An electromagnetic wave detection apparatus comprising:
an electromagnetic wave source; and
the electromagnetic wave detector according to claim 1, wherein an image of an object arranged between the electromagnetic wave source and the electromagnetic wave detector is generated.

22. An inspection apparatus comprising:
the electromagnetic wave detection apparatus according to claim 21; and
a detector configured to determine quality of an object using an image generated by the electromagnetic wave detection apparatus.

* * * * *